United States Patent
Sakuma et al.

(10) Patent No.: US 10,472,333 B2
(45) Date of Patent: Nov. 12, 2019

(54) P2X4 RECEPTOR ANTAGONIST

(71) Applicants: NIPPON CHEMIPHAR CO., LTD., Tokyo (JP); KYUSHU UNIVERSITY, Fukuoka (JP)

(72) Inventors: Shogo Sakuma, Saitama (JP); Kunio Kobayashi, Saitama (JP); Masatoshi Ushioda, Tokyo (JP); Toshiyasu Imai, Tokyo (JP); Kazuhide Inoue, Tokyo (JP)

(73) Assignees: NIPPON CHEMIPHAR CO., LTD., Tokyo (JP); KYUSHU UNIVERSITY, Fukuoka (JP)

( * ) Notice: Subject to any disclaimer, the term of this patent is extended or adjusted under 35 U.S.C. 154(b) by 0 days.

(21) Appl. No.: 16/039,947

(22) Filed: Jul. 19, 2018

(65) Prior Publication Data

US 2018/0319752 A1    Nov. 8, 2018

Related U.S. Application Data

(63) Continuation of application No. 14/903,343, filed as application No. PCT/JP2014/068540 on Jul. 11, 2014, now Pat. No. 10,150,744.

(30) Foreign Application Priority Data

Jul. 12, 2013   (JP) .................................. 2013-146212

(51) Int. Cl.
    C07D 243/10    (2006.01)
    C07D 401/12    (2006.01)
    C07D 401/14    (2006.01)

(52) U.S. Cl.
    CPC ......... *C07D 243/10* (2013.01); *C07D 401/12* (2013.01); *C07D 401/14* (2013.01)

(58) Field of Classification Search
    CPC ... C07D 243/10; C07D 401/12; C07D 401/14
    See application file for complete search history.

(56) References Cited

U.S. PATENT DOCUMENTS

2005/0074819 A1    4/2005  Inoue et al.

FOREIGN PATENT DOCUMENTS

| AU | 2013208536 | 7/2013 |
|----|------------|--------|
| CA | 2 809 113  | 2/2012 |
| CA | 2 840 336  | 11/2012 |
| EP | 2 397 480  | 12/2011 |
| EP | 2 803 662  | 11/2014 |
| EP | 3 020 717  | 5/2016 |
| WO | 2004/085440 | 10/2004 |
| WO | 2008/023847 | 2/2008 |
| WO | 2010/090300 | 8/2010 |
| WO | 2010/093061 | 8/2010 |
| WO | 2012/008478 | 1/2012 |
| WO | 2012/011549 | 1/2012 |
| WO | 2012/014910 | 2/2012 |
| WO | 2012/017876 | 2/2012 |
| WO | 2012/060397 | 5/2012 |
| WO | 2012/161301 | 11/2012 |
| WO | 2013/105608 | 7/2013 |

OTHER PUBLICATIONS

International Search Report issued with respect to Application No. PCT/JP2014/068540, dated Oct. 14, 2014.
International Preliminary Report on Patentability issued with respect to Application No. PCT/JP2014/068540, dated Jan. 12, 2016.
European Search Report issued with respect to Application No. 14822945.3, dated Sep. 11, 2016.
Buell et al., "An antagonist-insensitive P2x receptor expressed in epithelia and brain", The EMBO Journal, vol. 15, No. 1, pp. 55-62, 1996.
Seguela et al., "A Novel Neuronal P2x ATP Receptor Ion Channel with Widespread Distribution in the Brain", The Journal of Neuroscience, Jan. 15, 1990, pp. 448-455.
Bo et al., "A P2x purinoceptor cDNA conferring a novel pharmacological profile", FEBS Letters 375, 1995, pp. 129-133.
Soto et al., "P2X4: An ATP-activated ionotropic receptor cloned from rat brain", Proc. Natl. Acad. Sci. USA, vol. 93, pp. 3684-3688, 1996.

(Continued)

*Primary Examiner* — Bruck Kifle
(74) *Attorney, Agent, or Firm* — Greenblum & Bernstein, P.L.C.

(57) ABSTRACT

Compounds represented by the following general formula (I), which has a P2X4 receptor antagonistic activity (in the formula, $R^1$, $R^2$ and $R^3$ represent hydrogen atom, an alkyl group having 1 to 8 carbon atoms, an alkoxy group having 1 to 8 carbon atoms, a halogen atom, and the like, X represents C or N, Y represents N or C(=O), provided that when X is C, Y represents N, and when X is N, Y represents C(=O), the double line consisting of the solid line and the broken line represents a single bond or double bond, n represents an integer of 0 to 6, Z represents O, S, or an atomic bond, and A represents benzene ring, pyridine ring, and the like).

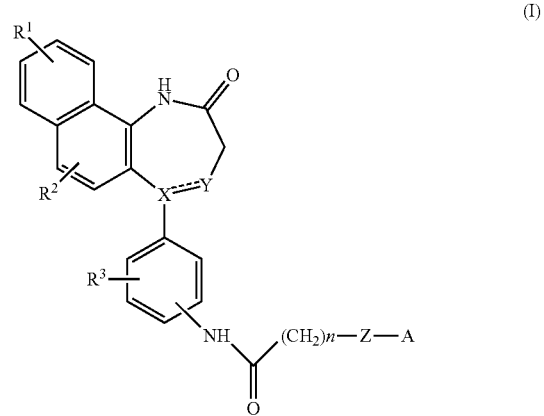

(I)

11 Claims, 1 Drawing Sheet

(56) References Cited

OTHER PUBLICATIONS

Wang et al., "Cloning and Pharmacological Characterization of a Fourth P2X Receptor Subtype Widely Expressed in Brain and Peripheral Tissues Including Various Endocrine Tissues", Biochemical and Biophysical Research Communications, vol. 220, pp. 196-202, 1996.

M. Tsuda et al., "P2X4 receptors induced in spinal microglia gate tactile allodynia after nerve injury", Nature, vol. 424, pp. 778-783, 2003.

Jeffrey A. M. Coull et al., "BDNF from microglia causes the shift in neuronal anion gradient underlying neuropathic pain", Nature, vol. 438, pp. 1017-1021, 2005.

Kenichiro Nagata et al., "Inhibitory effects of antidepressants on P2X4 receptor: a novel mechanism in neuropathic pain relief", The 49th Convention of the Japanese Society for Neurochemistry, Program Lecture Abstract P3-N-114, 2006.

European Office Action from Patent Application No. 14822945.3 dated Oct. 12, 2017.

Examination Report from Australian Patent Application No. 2014288115 dated Nov. 16, 2017.

European Search Report, European Patent Office, Application No. 19181298.1, dated Jul. 24, 2019.

Japanese Office Action, Japanese Patent Office, Application No. 2018-132540, dated Apr. 3, 2019, with English Machine Translation.

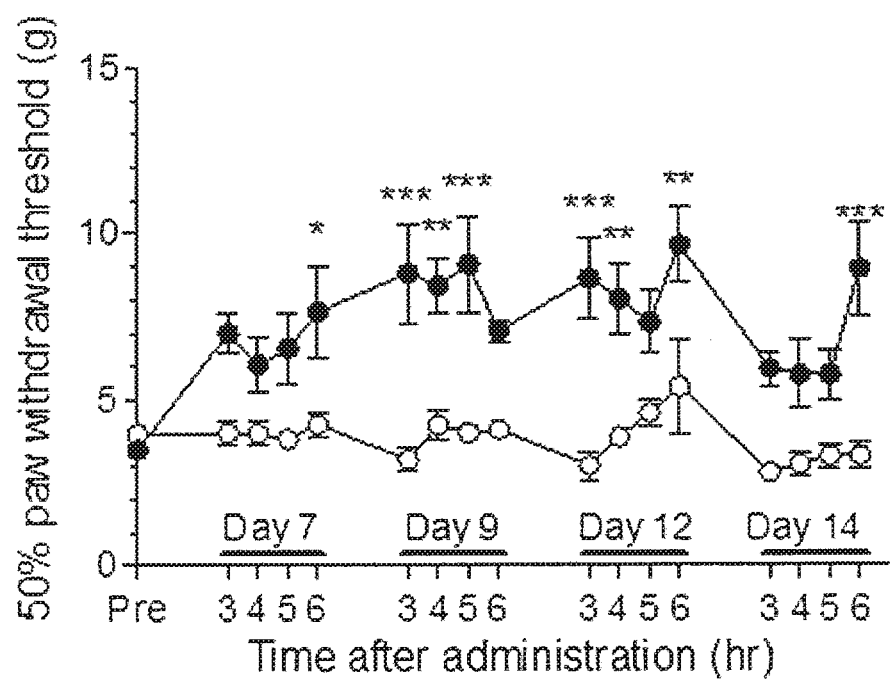
Mean±S.E.M. (n=5-10) ***; P<0.001 (60 mg/kg/day),
*; P<0.05 (60 mg/kg/day) vs vehicle group.
Two-Way ANOVA Bonferroni post tests.

P2X4 RECEPTOR ANTAGONIST

The present application is a Continuation of U.S. application Ser. No. 14/903,343, which is a National stage of International Patent Application No. PCT/JP2014/068540 filed Jul. 11, 2014, which claims priority to Japanese Application No. 2013-146212 filed Jul. 12, 2013. The disclosures of U.S. application Ser. No. 14/903,343 and International Patent Application No. PCT/JP2014/068540 are incorporated by reference herein in their entireties.

TECHNICAL FIELD

The present invention relates to a diazepine derivative having a P2X4 receptor antagonist activity.

BACKGROUND ART

The ATP receptors are roughly classified into the P2X family of the ion channel type receptors, and the P2Y family of the G protein coupling type receptors, and seven kinds (P2X1 to P2X7) and eight kinds (P2Y1, P2Y2, P2Y4, P2Y6, and P2Y11 to P2Y14) of subtypes have so far been reported for each family.

The P2X4 receptor (Genebank No. X87763), a subtype of the P2X family, has been reported to be widely expressed in the central nervous system, and the like (Non-patent documents 1 to 5).

The onset mechanisms of chronic or intractable pains including neuropathic pain have not been fully elucidated, and if non-steroidal anti-inflammatory drugs (NSAIDs) and morphine are not effective for such a pain, no therapy is available for that pain. Therefore, very heavy physical and mental burdens are given to patients and people around them. Neuropathic pain is often caused by injury of a peripheral nerve or the central nerve, and it is caused by, for example, after-trouble of operation, cancer, spinal cord injury, herpes zoster, diabetic neuritis, trigeminal neuralgia, and the like.

Recently, Inoue et al. verified the involvement of the P2X receptor in neuropathic pain by using a spinal nerve-damaged animal model in which allodynia can be detected, and they described that nerve-damaged type unusual pain (especially allodynia) is induced through the P2X4 receptor expressed in the microglia cells of the spinal cord (Non-patent documents 6 and 7, and Patent document 1).

Therefore, a substance that inhibits the activity of the P2X4 receptor is expected to be a prophylactic or therapeutic agent for pains of nociceptive pain, inflammatory pain, and neuropathic pain caused by after-trouble of operation, cancers, spinal cord injury, herpes zoster, diabetic neuritis, trigeminal neuralgia, and the like.

Patent document 2 reported that a benzofuro-1,4-diazepin-2-one derivative represented by the following general formula (A):

[Formula 1]

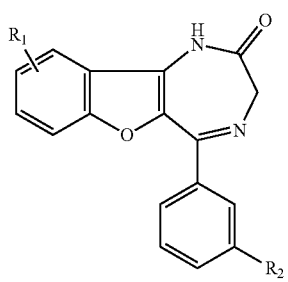

(A)

(in the formula, $R_1$ is a halogen, and $R_2$ is hydrogen, a halogen, nitro, cyano, C(O)—$OR_3$, C(O)—$NR_4R_5$, $SO_2$—$OR_3$, or $SO_2$—$NR_4R_5$, or $R_1$ is hydrogen, and $R_2$ is a halogen, nitro, cyano, C(O)—$OR_3$, C(O)—$NR_4R_5$, $SO_2$—$OR_3$, or $SO_2$—$NR_4R_5$) has a P2X4 receptor antagonist activity.

It was also reported that paroxetine, which is an antidepressant, has a P2X4 receptor antagonist activity (Non-patent document 8).

The inventors of the present invention also found that a naphtho[1,2-e][1,4]diazepin-2-one derivative represented by the following formula (B):

[Formula 2]

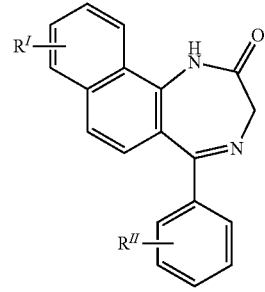

(B)

(in the formula, $R^I$ represents hydrogen, a lower alkyl, a lower alkoxy, and the like, and $R^{II}$ represents hydroxy, a lower alkyl, a lower alkoxy, tetrazolyl group, and the like).

a naphtho[1,2-b][1,4]diazepin-2,4-dione derivative represented by the Mowing general formula (C):

[Formula 3]

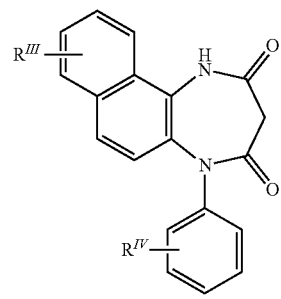

(C)

(in the formula, $R^{III}$ represents hydrogen, a lower alkyl, a lower alkoxy, and the like, and $R^{IV}$ represents hydrogen, a lower alkyl, a lower alkoxy, tetrazolyl group, and the like), and related compounds thereof have a P2X4 receptor antagonist activity, and filed patent applications therefor (Patent documents 3 to 10).

PRIOR ART REFERENCES

Patent Documents

Patent document 1: Published U.S. Patent Application No. 20050074819
Patent document 2: WO2004/085440
Patent document 3: WO2008/023847
Patent document 4: WO201.0/093061

Patent document 5: WO2010/090300
Patent document 6: WO2012/008478
Patent document 7: WO2012/11549
Patent document 8: WO2012/14910
Patent document 9: WO2012/17876
Patent document 10: WO2013/105608

Non-Patent Documents

Non-patent document, 1: Buell et al. (1996) EMBO J., 15:55.62
Non-patent document 2: Seguela et al. (1996) J. Neurosci., 16:448-455
Non-patent document 3: Bo et al. (1995) FEBS Lett., 375:129-133
Non-patent document 4: Soto et al, (1996) Proc. Natl. Acad. Sci. USA., 93:3684-3788
Non-patent document 5: Wang et al. (1996) Biochem. Res. Commun., 220:196-202
Non-patent document 6: M. Tsuda et al. (2003) Nature, 424, 778-783
Non-patent document 7: Jeffrey A. M. Coull et al. (2005) Nature, 438, 1017-1021
Non-patent document 8: The 49th Convention of The Japanese Society for
Neurochemistry (2006), Program Lecture Abstract P3-N-114

SUMMARY OF THE INVENTION

Object to be Achieved by the Invention

So far to date, any safe medicament in the form of a preparation for oral administration has not been provided which can be easily taken and has a superior P2X4 receptor antagonist activity.

An object of the present invention is to provide a diazepine derivative represented by the following general formula (I) and having a P2X4 receptor antagonist activity.

Means for Achieving the Object

The present invention thus relates to a compound represented by the following general formula (I), a tautomer or a stereoisomer of the compound, or a pharmacologically acceptable salt thereof, or a solvate of any of the foregoing:

[Formula 4]

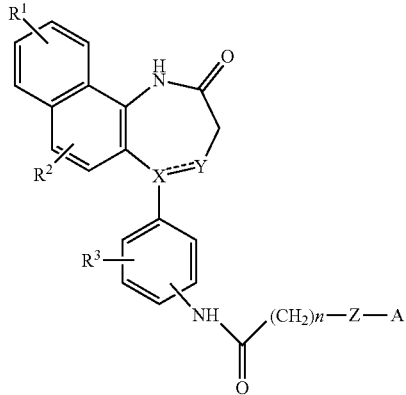

(I)

(wherein, in the formula, $R^1$, $R^2$ and $R^3$ may be the same or different, and represent hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, or a dialkylamino group having 2 to 8 carbon atoms, X represents C or N,
Y represents N or C(=O),
provided that when X is C, Y represents N, and
when X is N, I represents C(=O),
the double line consisting of the solid line and the broken line represents a single bond or double bond,
n represents an integer of 0 to 6,
Z represents O, S, or an atomic bond, and
A represents benzene ring, pyridine ring, piperazine ring, piperidine ring, or morpholine ring, which may have the same or different 1 to 5 substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and $N(R^4)(R^5)$, as a substituent, wherein $R^4$ and $R^5$ may be the same or different, and represent an alkyl group having 1 to 8 carbon atoms, or $R^4$ and $R^5$ bind to represent, together with the nitrogen atom to which $R^4$ and $R^5$ bind, a 5- to 7-membered ring, which may further contain oxygen atom, or sulfur atom as a ring-constituting heteroatom).

The present invention also relates to a P2X4 receptor antagonist containing a compound represented by the aforementioned general formula (I), a tautomer or a stereoisomer of the compound, or a pharmacologically acceptable salt thereof, or a solvate of any of the foregoing as an active ingredient.

The present invention further relates to a prophylactic or therapeutic agent for nociceptive pain, inflammatory pain, or neuropathic pain containing a compound represented by the aforementioned general formula (I), a tautomer or a stereoisomer of the compound, or a pharmacologically acceptable salt thereof, or a solvate of any of the foregoing as an active ingredient.

BRIEF DESCRIPTION OF THE DRAWING

FIG. 1 shows results of measurement of the analgesic activity of the compound of the present invention (Example 28).

MODES FOR CARRYING OUT THE INVENTION

Hereafter, the present invention will be explained in detail.

In this specification, examples of the alkyl group having 1 to 8 carbon atoms include methyl group, ethyl group, propyl group, isopropyl group, butyl group, i-butyl group, t-butyl group, pentyl group, hexyl group, and the like.

Examples of the cycloalkyl group having 3 to 8 carbon atoms include cyclopropyl group, cyclohexyl group, and the like.

Examples of the alkenyl group having 2 to 8 carbon atoms include allyl group, and e like.

Examples of the alkoxy group having 1 to 8 carbon atoms include methoxy group, ethoxy group, propoxy group, isopropoxy group, butoxy group, i-butoxy group, t-butoxy group, pentyloxy group, hexyloxy group, and the like.

Examples of the alkyl group having 1 to 8 carbon atoms and substituted with 1 to 3 halogen atoms include methyl group, ethyl group, propyl group, isopropyl group, butyl group, t-butyl group, and the like, which are substituted with 1 to 3 of halogen atoms such as fluorine atom, chlorine atom, and bromine atom, and preferred examples include trifluoromethyl group, chloromethyl group, 2-chloroethyl group, 2-bromoethyl group, 2-fluoroethyl group, and the like.

Examples of the alkoxy group having 1 to 8 carbon atoms and substituted with 1 to 3 halogen atoms include methoxy group, ethoxy group, propoxy group, isopropoxy group, butoxy group, t-butoxy group, and the like, which are substituted with 1 to 3 of halogen atoms such as fluorine atom, chlorine atom, and bromine atom, and preferred examples include trifluoromethoxy group, chloromethoxy group, 2-chloroethoxy group, 2-bromoethoxy group, 2-fluoroethoxy group, and the like.

Examples of the halogen atom include iodine atom, fluorine atom, chlorine atom, bromine atom, and the like.

Examples of the alkylamino group having 1 to 8 carbon atoms include methylamino group, ethylamino group, and the like.

Examples of the dialkylamino group having 2 to 8 carbon atoms include dimethylamino group, diethylamino group, and the like.

Examples of the 5- to 7-membered ring formed by $R^4$ and $R^5$ binding together, together with the nitrogen atom to which $R^4$ and $R^5$ bind, which may further contain oxygen atom, or sulfur atom as a ring-constituting heteroatom, include morpholin-4-yl, 1H-pyrrol-1-yl, pyrrolidin-1-yl, and the like.

$R^1$ mentioned above may have the same or different 1 to 4 substituents.

$R^2$ mentioned above may have the same or different 1 or 2 substituents.

$R^3$ mentioned above may have the same or different 1 to 4 substituents.

As the compounds of the present invention represented by the aforementioned general formula (I), the compounds mentioned below are preferred.

(1)
The compound represented by the aforementioned general formula (I), a tautomer or a stereoisomer of the compound, or a pharmacologically acceptable salt thereof, or a solvate of any of the foregoing, wherein A is benzene ring, pyridine ring, piperazine ring, piperidine ring, or morpholine ring, which may have the same or different 1 to 5 substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, as a substituent.

(2)
The compound represented by the aforementioned general formula (I), a tautomer or a stereoisomer of the compound, or a pharmacologically acceptable salt thereof, or a solvate of any of the foregoing, wherein A is benzene ring, or pyridine ring, which may have the same or different 1 to 5 substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, amino group, an alkylamino group having 1 to 8 carbon atoms, and a dialkylamino group having 2 to 8 carbon atoms, as a substituent.

(3)
The compound represented by the aforementioned general formula (I), a tautomer or a stereoisomer of the compound, or a pharmacologically acceptable salt thereof, or a solvate of any of the foregoing, wherein A is benzene ring, which may have the same or different 1 to 5 substituents selected from an alkyl group having 1 to 8 carbon atoms, an alkoxy group having 1 to 8 carbon atoms, a halogen atom, hydroxyl group, amino group, an alkylamino group having 1 to 8 carbon atoms, and a dialkylamino group having 2 to 8 carbon atoms, as a substituent.

(4)
The compound represented by the aforementioned general formula (I), a tautomer or a stereoisomer of the compound, or a pharmacologically acceptable salt thereof, or a solvate of any of the foregoing, wherein A is pyridine ring having $N(R^4)(R^5)$ (in the formula. $R^4$ and $R^5$ bind to represent, together with the nitrogen atom to which $R^4$ and $R^5$ bind, a 5- to 7-membered ring, which may further contain oxygen atom, or sulfur atom as a ring-constituting heteroatom), as a substituent.

(5)
The compound represented by the aforementioned general formula (I), a tautomer or a stereoisomer of the compound, or a pharmacologically acceptable salt thereof, or a solvate of any of the foregoing, wherein A is pyridine ring having a substituent selected from morpholin-4-yl, 1H-pyrrol-1-yl, and pyrrolidin-1-yl, as a substituent, (6)
The compound represented by the aforementioned general formula (I) or the compound according to any one of (1) to (5) mentioned above, a tautomer or a stereoisomer of the compound, or a pharmacologically acceptable salt thereof, or a solvate of any of the foregoing, wherein $R^1$, $R^2$ and $R^3$ may be the same or different, and represent hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, or a halogen atom.

(7)
The compound represented by the aforementioned general formula (I) or the compound according to any one of (1) to (5) mentioned above, a tautomer or a stereoisomer of the compound, or a pharmacologically acceptable salt thereof, or a solvate of any of the foregoing, wherein $R^1$, $R^2$ and $R^3$ may be the same or different, and are hydrogen atom, or a halogen atom.

(8)
The compound represented by the aforementioned general formula (I) or the compound according to any one of (1) to (7) mentioned above, a tautomer or a stereoisomer of the compound, or a pharmacologically acceptable salt thereof, or a solvate of any of the foregoing, wherein n is 0.

(9)

The compound represented by the aforementioned general formula (I) or the compound according to any one of (1) to (7) mentioned above, a tautomer or a stereoisomer of the compound, or a pharmacologically acceptable salt thereof, or a solvate of any of the foregoing, wherein n is 1 or 2.

(10)

The compound represented by the aforementioned general formula (I) or the compound according to any one of (1) to (9) mentioned above, a tautomer or a stereoisomer of the compound, or a pharmacologically acceptable salt thereof, or a solvate of any of the foregoing, wherein Z is an atomic bond.

(11)

The compound represented by the aforementioned general formula (I), a tautomer or a stereoisomer of the compound, or a pharmacologically acceptable salt thereof, or a solvate of any of the foregoing, wherein:

$R^1$, $R^2$ and $R^3$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, or hydroxyl group, X is N, Y is C(=O), the double line consisting of the solid line and the broken line is a single bond, n is 0, Z is an atomic bond, and A is benzene ring, or pyridine ring, which may have the same or different 1 to 3 substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, amino group, an alkylamino group having 1 to 8 carbon atoms, and $N(R^4)(R^5)$, as a substituent, wherein $R^4$ and $R^5$ may be the same or different, and represent an alkyl group having 1 to 8 carbon atoms, or $R^4$ and $R^5$ bind to represent, together with the nitrogen atom to which $R^4$ and $R^5$ bind, morpholine ring, pyrrole ring, or pyrrolidine ring.

(12)

The compound represented by the aforementioned general formula (I), a tautomer or a stereoisomer of the compound, or a pharmacologically acceptable salt thereof, or a solvate of any of the foregoing, wherein:

$R^1$, $R^2$ and $R^3$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, or hydroxyl group, X is C, Y is N, the double line consisting of the solid line and the broken line is a double bond, n is an integer of 0 to 3, Z is an atomic bond, and A is benzene ring, or pyridine ring, which may have the same or different 1 to 3 substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, amino group, an alkylamino group having 1 to 8 carbon atoms, and $N(R^4)(R^5)$, as a substituent, wherein $R^4$ and $R^5$ may be the same or different, and represent an alkyl group having 1 to 8 carbon atoms, or $R^4$ and $R^5$ bind to represent, together with the nitrogen atom to which $R^4$ and $R^5$ bind, morpholine ring, pyrrole ring, or pyrrolidine ring.

(13)

The compound represented by the aforementioned general formula (I) or the compound according to any one of (1) to (12) mentioned above, a tautomer or a stereoisomer of the compound, or a pharmacologically acceptable salt thereof, or a solvate of any of the foregoing, wherein X and NHC(=O) are mutually present at the para-positions on the phenyl group.

Examples of the pharmacologically acceptable salts of the compounds represented by the aforementioned general formula (I) include hydrochlorides, mesylates, and alkali metal salts such as those of sodium, potassium, and lithium.

Further, there may be stereoisomers of the compounds of the present, invention, such as cis- and trans-isomers, optically active substances, and racemates, and all of these substances fall within the scope of the present invention.

The synthetic schemes of the compounds of the present invention represented by the aforementioned general formula (I) are shown below.

(I) Synthesis Method of naphtho[1,2-b][1,4]diazepine-2,4-dione derivatives (1) Compounds represented by the aforementioned general formula (I) in which X is N, Y is C(=O), and the double line consisting of the solid line and the broken line is a single bond Synthesis method

[Formula 5]

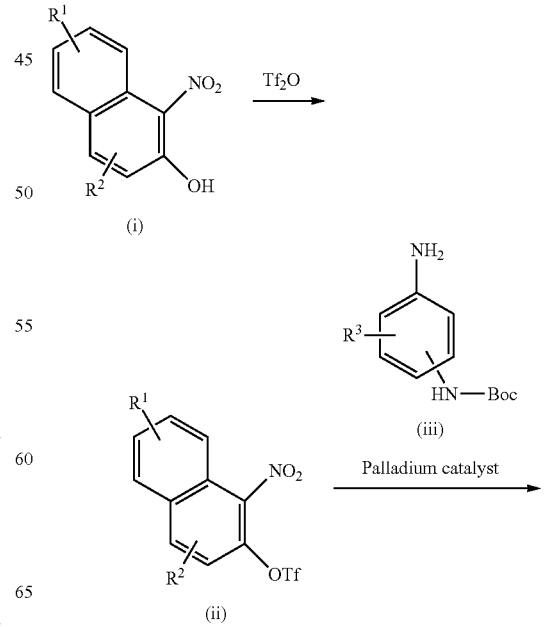

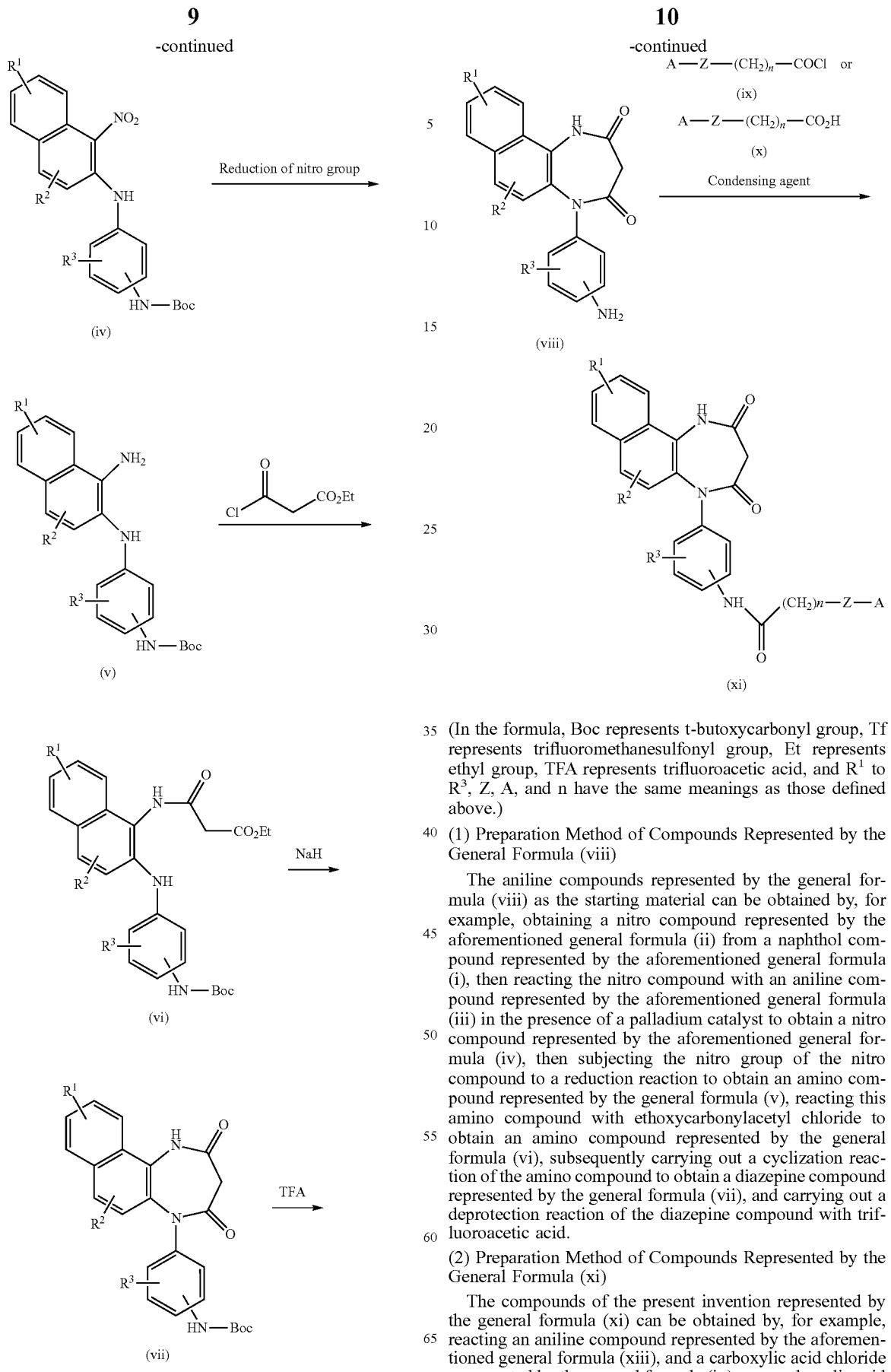

(In the formula, Boc represents t-butoxycarbonyl group, Tf represents trifluoromethanesulfonyl group, Et represents ethyl group, TFA represents trifluoroacetic acid, and $R^1$ to $R^3$, Z, A, and n have the same meanings as those defined above.)

(1) Preparation Method of Compounds Represented by the General Formula (viii)

The aniline compounds represented by the general formula (viii) as the starting material can be obtained by, for example, obtaining a nitro compound represented by the aforementioned general formula (ii) from a naphthol compound represented by the aforementioned general formula (i), then reacting the nitro compound with an aniline compound represented by the aforementioned general formula (iii) in the presence of a palladium catalyst to obtain a nitro compound represented by the aforementioned general formula (iv), then subjecting the nitro group of the nitro compound to a reduction reaction to obtain an amino compound represented by the general formula (v), reacting this amino compound with ethoxycarbonylacetyl chloride to obtain an amino compound represented by the general formula (vi), subsequently carrying out a cyclization reaction of the amino compound to obtain a diazepine compound represented by the general formula (vii), and carrying out a deprotection reaction of the diazepine compound with trifluoroacetic acid.

(2) Preparation Method of Compounds Represented by the General Formula (xi)

The compounds of the present invention represented by the general formula (xi) can be obtained by, for example, reacting an aniline compound represented by the aforementioned general formula (xiii), and a carboxylic acid chloride represented by the general formula (ix), or a carboxylic acid represented by the general formula (x) in the presence or absence of a condensing agent in a solvent that does not participate in the reaction.

(II) Synthesis Method of Naphth[1,2-e][1,4]diazepine-2-dione derivatives (1) Compounds represented by the aforementioned general formula (I) in which X is C, Y is N, and the double line consisting of the solid line and the broken line is a double bond Synthesis method

[Formula 6]

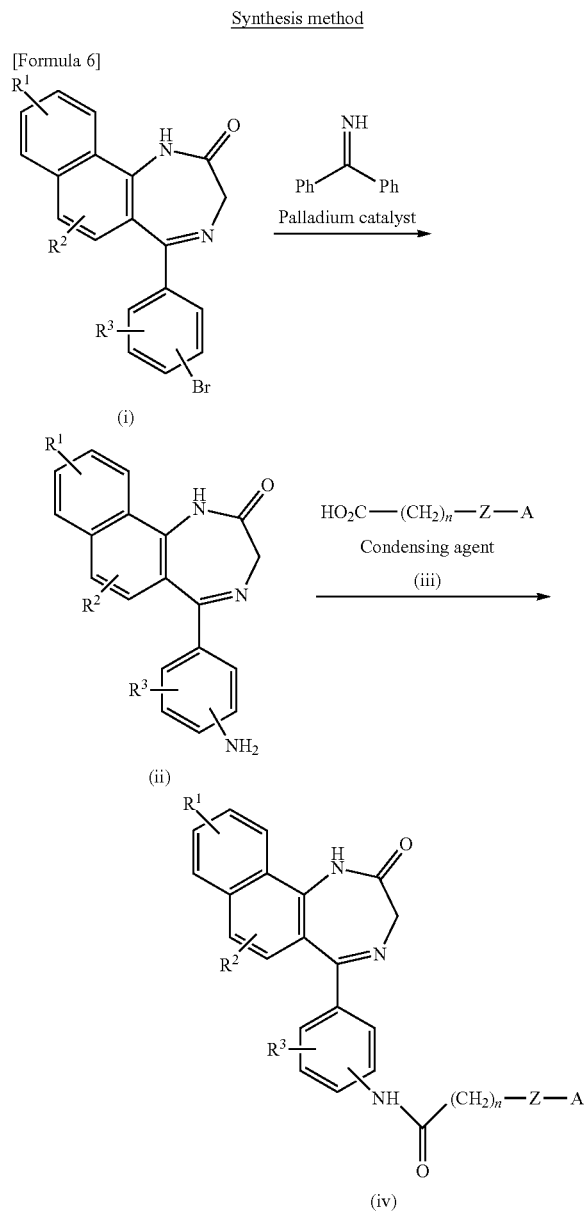

(In the formula, Ph represents phenyl group, and $R^1$ to $R^3$, Z, A, and n have the same meanings as those defined above.)

(3) Amino Compounds Represented by the Aforementioned General Formula (ii)

The amino compounds represented by the aforementioned general formula (ii) can be obtained by reacting a bromo compound represented by the aforementioned general formula (i) with benzophenone imine in the presence of a palladium catalyst.

(4) Diazepine Compounds Represented by the Aforementioned General Formula (iv)

The diazepine compounds represented by the aforementioned general formula (iv) can be obtained by reacting an amino compound represented by the aforementioned general formula (ii), and a carboxylic acid represented by general formula (iii) in the presence or absence of a condensing agent in a solvent that does not participate in the reaction.

The compounds of the present invention represented by the aforementioned general formula (I) can be prepared by referring to the aforementioned synthesis methods and the examples mentioned later, as well as the aforementioned patent documents, prior art references, and the like.

Examples of typical compounds of the present invention obtained as described above are mentioned below.

(Examples of Typical Compounds 1)

[Formula 7]

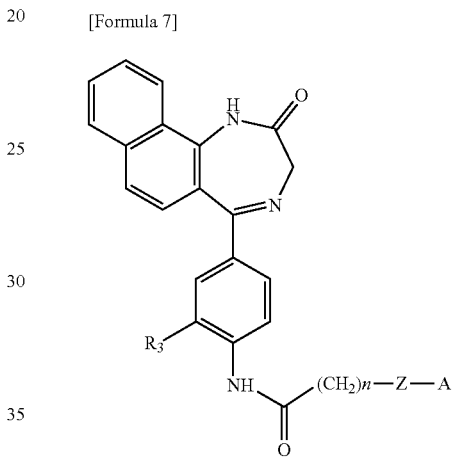

(In the formula, $R^3$, A, Z, and n are as mentioned in Tables 1 and 2)

TABLE 1

| $R^3$ | n | Z | A |
|---|---|---|---|
| H | 2 | Bond | Pyridin-2-yl |
| H | 0 | Bond | (2-Et, 3-OH)Phenyl |
| H | 0 | Bond | (2-Et)Pyridin-3-yl |
| H | 0 | Bond | (2-Et, 6-OH)Phenyl |
| H | 0 | Bond | (3-Et)Pyridin-2-yl |
| H | 1 | O | Pyridin-2-yl |
| H | 1 | Bond | (2-OMe)Phenyl |
| H | 2 | Bond | Pyridin-3-yl |
| H | 2 | Bond | Phenyl |
| H | 2 | Bond | Cyclohexyl |
| H | 1 | Bond | Pyridin-2-yl |

TABLE 2

| $R^3$ | n | Z | A |
|---|---|---|---|
| H | 1 | Bond | Pyridin-3-yl |
| H | 1 | Bond | Pyridin-4-yl |
| H | 3 | Bond | Pyridin-2-yl |
| H | 1 | Bond | (2-NMe$_2$)Phenyl |
| OH | 1 | O | Pyridin-2-yl |
| OMe | 2 | O | Pyridin-2-yl |
| CN | 2 | Bond | Pyridin-2-yl |
| Me | 2 | Bond | Pyridin-2-yl |
| CF$_3$ | 1 | Bond | Pyridin-2-yl |

TABLE 2-continued

| R³ | n | Z | A |
|----|---|---|---|
| F | 2 | Bond | Pyridin-2-yl |
| H | 0 | Bond | (2-NMe₂)Pyridin-3-yl |
| F | 2 | Bond | Phenyl |

(Examples of Typical Compounds 2)

[Formula 8]

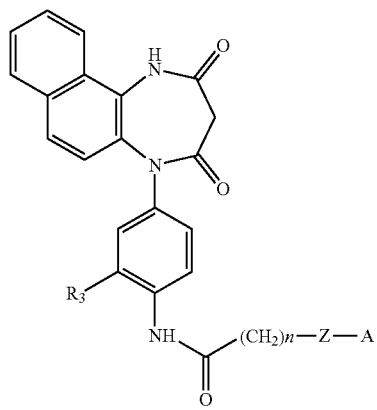

(In the formula, R³, A, Z, and n are as mentioned in Tables 3 and 4.)

TABLE 3

| R³ | n | Z | A |
|----|---|---|---|
| H | 2 | Bond | Pyridin-3-yl |
| H | 2 | Bond | Pyridin-4-yl |
| F | 0 | Bond | (2-tBu)Phenyl |
| H | 2 | Bond | Pyridin-2-yl |
| H | 0 | Bond | (2-NMe₂)Pyridin-3-yl |
| H | 2 | Bond | Cyclohexyl |
| H | 1 | Bond | Pyridin-2-yl |
| H | 1 | Bond | Pyridin-3-yl |

TABLE 4

| R³ | n | Z | A |
|----|---|---|---|
| H | 1 | Bond | Pyridin-4-yl |
| H | 3 | Bond | Pyridin-2-yl |
| H | 1 | Bond | (2-NMe₂)Phenyl |
| OH | 1 | O | Pyridin-2-yl |
| OMe | 2 | O | Pyridin-2-yl |
| CN | 2 | Bond | Pyridin-2-yl |
| Me | 2 | Bond | Pyridin-2-yl |
| CF₃ | 1 | Bond | Pyridin-2-yl |
| F | 2 | Bond | Pyridin-2-yl |
| F | 2 | Bond | Phenyl |

(Examples of Typical Compounds 3)

[Formula 9]

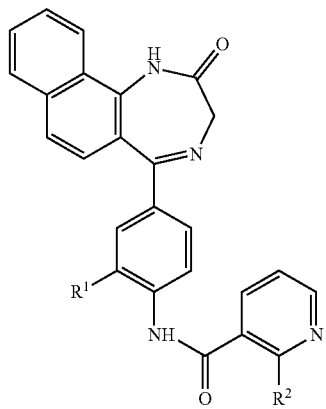

(In the formula, R¹, R², and type of salt are as mentioned in Tables 5 and 6)

TABLE 5

| R¹ | R² | Salt |
|----|----|------|
| H | NMe₂ | 2HCl |
| H | NMe₂ | 2MsOH |
| H | 1H-Pyrrol-1-yl | 2HCl |
| H | Morpholin-4-yl | 2HCl |
| H | Pyrrolidin-1-yl | 2HCl |
| H | iPr | 2HCl |
| H | iPrNH | 2HCl |
| F | NMe₂ | |
| OH | NMe₂ | |
| F | 1H-Pyrrol-1-yl | |
| OH | Morpholin-4-yl | |

TABLE 6

| R¹ | R² | Salt |
|----|----|------|
| F | Pyrrolidin-1-yl | |
| OH | iPr | |
| F | iPrNH | |
| H | NEt₂ | |
| H | NHEt | |
| F | NHMe | |
| Me | 1H-Pyrrol-1-yl | |
| Me | Morpholin-4-yl | |
| Me | Pyrrolidin-1-yl | |

(Examples of Typical Compounds 4)

[Formula 10]

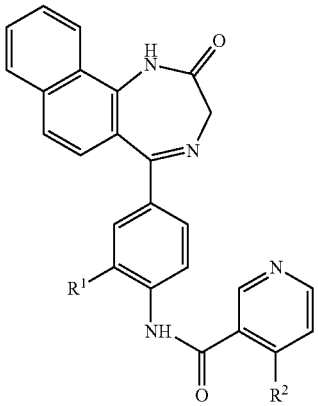

(In the formula, $R^1$, $R^2$ and type of salt are as mentioned in Table 7.)

TABLE 7

| $R^1$ | $R^2$ | Salt |
| --- | --- | --- |
| H | NMe$_2$ | 2HCl |
| H | 1H-Pyrrol-1-yl | |
| H | Morpholin-4-yl | |
| H | Pyrrolidin-1-yl | |
| H | iPr | |
| H | iPrNH | |
| F | NMe$_2$ | |

(Examples of Typical Compounds 5)

[Formula 11]

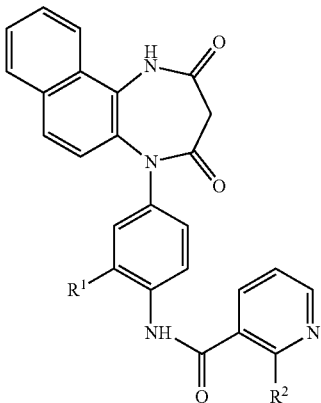

(In the formula, $R^1$, $R^2$ and type of salt are as mentioned in Table 8.)

TABLE 8

| $R^1$ | $R^2$ | Salt |
| --- | --- | --- |
| H | NMe$_2$ | HCl |
| H | Morpholin-4-yl | HCl |
| H | Pyrrolidin-1-yl | |
| H | iPr | |
| H | iPrNH | |

TABLE 8-continued

| $R^1$ | $R^2$ | Salt |
| --- | --- | --- |
| F | NMe$_2$ | |
| OH | NMe$_2$ | |
| F | 1H-pyrrol-1-yl | |
| OH | Morpholin-4-yl | |
| F | Pyrrolidin-1-yl | |
| OH | iPr | |
| F | iPrNH | |
| H | NEt$_2$ | |
| H | NHEt | |
| F | NHMe | |
| Me | 1H-pyrrol-1-yl | |
| Me | Morpholin-4-yl | |

Hereafter, the pharmacological efficacies of the compounds of the present invention will be described.

The P2X4 receptor antagonist activities of the compounds of the present invention were measured as follows.

The ATP receptor (human P2X4) was introduced into the 1321N1 cells, and the cells were used as a stable ATP receptor expression system. The P2X4-expressing 1321N1 cells were seeded on a 90-well plate, cultured under the conditions of 37° C. and 5% $CO_2$ for 24 hours, and used for calcium measurement. Fura-2 AM, which is a calcium fluorescent indicator, was dissolved in an extracellular fluid for calcium imaging, and the seeded cells were treated with the solution, and left standing at room temperature for 45 minutes so that Fura-2 AM was incorporated into the cells. For the measurement, a microplate reader, Fluostar Optima (BMG Labtech), was used. The light emitted from a xenon lamp was passed through 340 nm and 380 nm filters, respectively, and irradiated on the cells, fluorescences of 510 nm, $F_{340}$ and $F_{380}$, emitted from the cells were measured, and change of the ratio $F_{340}/F_{380}$ was used as an index of change of intracellular calcium level. The measurement was performed by adding ATP to each well at a final concentration of 1 μM, and observing the ATP-induced $Ca^{2+}$ response over time. In the measurement, a treatment with a test substance was performed 15 minutes before the addition of ATP, and the inhibitory activity of the test substance was calculated by comparison of the result with the result obtained in the absence of the test substance.

As clearly seen from the results for the compounds of Examples 25 and 26, the compounds of the present invention showed superior P2X4 receptor antagonist activity (Tables 9 and 10).

P2X receptor family selectivity of the compound of the present invention (compound described in Example 15) was measured. As a result, the compound of the present invention showed high selectivity for the P2X4 receptor as shown in Table 11 (Example 27).

Further, analgesic activity of the compound of the present invention (compound described in Example 15) was measured by using rat neuropathic pain model (modified Chung model). As a result, it became clear that the compound of the present invention has superior analgesic activity (Example 28, FIG. 1).

Therefore, the compounds represented by the aforementioned general formula (I), tautomers or stereoisomers of the compounds, or pharmacologically acceptable salts thereof, or solvates of any of the foregoing have a P2X4 receptor antagonist activity, and accordingly, it is considered that they are useful as prophylactic or therapeutic agents for pains of nociceptive pain, inflammatory pain, and neuropathic pain. More specifically, they are useful as prophylactic and therapeutic agents for pains accompanying various cancers, pains accompanying diabetic nerve damage, pains accompanying viral diseases such as herpes, arthrosis deformans, and the like. The prophylactic or therapeutic agent of the present invention may be used together with other medicaments if needed, and may be used together with, for example, opioid analgesics (morphine, fentanyl), sodium channel blockers (Novocain, lidocaine), NSAIDs (aspirin, ibuprofen), and the like. Further, when it is used for cancerous pain, it may be used together with, for example, anticancer agents such as anticancer chemotherapeutic agents.

The compounds of the present invention can be administered to a human by an appropriate administration method, such as oral administration or parenteral administration.

For manufacturing pharmaceutical preparations containing the compounds of the present invention, dosage forms such as tablets, granules, powders, capsules, suspensions, injections, and suppositories can be prepared by the methods usually used in the field of pharmaceutical manufacturing.

For manufacturing such preparations, in the case of tablets, for example, usual excipients, disintegrating agents, binders, lubricants, dyes, and the like are used. Examples of excipient include lactose, D-mannitol, crystalline cellulose, glucose, and the like, examples of disintegrating agent include starch, carboxymethylcellulose calcium (CMC—Ca), and the like, examples of lubricant include magnesium stearate, talc, and the like, and examples of binder include hydroxypropylcellulose (HPC), gelatin, polyvinylpyrrolidone (PVP), and the like. For manufacturing injection, solvents, stabilizers, dissolving aids, suspending agents, emulsifiers, soothing agents, buffering agents, preservatives, and the like are used.

As for the administration dose, the compounds of the present invention as the active ingredient can usually be administered to an adult in a daily dose of about 0.01 to 100 mg in the case of injection, or a daily dose of 1 to 2000 mg in the case of oral administration, but the close may be increased or decreased depending on age, symptoms, and the like.

The compounds of the present invention include highly safe compounds such as those not showing the hERG potassium ion channel inhibitory activity, and they are also superior P2X4 receptor antagonists that can be made into easily-taken preparations for oral administration. Therefore, they are useful as prophylactic and therapeutic agents for nociceptive pain, inflammatory pain, and neuropathic pain.

Hereafter, the present invention will be explained in more detail with reference to examples. However, the present invention is not limited to these examples.

Example 1

N-[4-(2-Oxo-2,3-dihydro-1H-naphtho[1,2-e][1,4]-diazepin-5-yl)phenyl]-3-(pyridin-2-yl)propionamide (1) 5-(4-Aminophenyl)-1H-naphtho[1,2-e][1,4]diazepin-2(3H)-one 5-(4-Bromophenyl)-1H-naphtho[1,2-e][1,4]diazepin-2(3H)-one (380 mg, 1.04 mmol) synthesized with reference to WO2008/023847A1, benzophenone imine (349 mg, 2.08 mmol), sodium tert-butoxide (200 mg, 2.08 mmol), palladium(II) acetate (23 mg, 0.104 mmol), and 4,5-bis(diphenylphosphino)-9,9-dimethylxanthene (60 mg, 0.208 mmol) were dissolved in anhydrous dioxane (5 mL), and the solution was stirred at 110° C. for 16 hours. The reaction mixture was left to cool, and then poured into water, and the resulting mixture was extracted with chloroform. The organic layer was washed with saturated brine, and dried over anhydrous sodium sulfate. The solvent was evaporated under reduced pressure, and the residue was purified by silica gel column chromatography (chloroform/methanol=100/1) to obtain the title compound (154 mg, yield 49%).

$^1$H NMR (DMSO-$d_6$, 400 MHz) δ: 3.67 (1H, d, J=10 Hz), 4.42 (1H, d, J=1.0 Hz), 5.57 (2H, s), 6.54 (2H, d, J=8 Hz), 7.24 (2H, d, J=8 Hz), 7.33 (1H, d, J=9 Hz), 7.6-7.8 (3H, m), 7.9-8.1 (1 h, m), 8.3-8.4 (1H, m), 10.67 (1H, br s)

(2) N-[4-(2-Oxo-2,3-dihydro-1H-naphtho[1,2-e][1,4]-diazepin-5-yl)phenyl]-3-(pyridin-2-yl)propionamide dihydrochloride 5-(4-Aminophenyl)-1H-naphtho[1,2-e][1,4]diazepin-2(3H)-one (100 mg, 0.330 mmol) obtained above, and 3-(pyridin-2-yl)propionyl chloride (60.0 mg, 0.360 mmol) was stirred at 80° C. for 12 hours in a pyridine solvent. The solvent was evaporated, then saturated aqueous sodium hydrogencarbonate was added to the residue, and the resulting mixture was extracted with an organic solvent. The organic layer was washed with saturated brine, and dried over anhydrous sodium sulfate. The solvent was evaporated under reduced pressure, and the residue was purified by silica gel chromatography, and then made into hydrochloride in a conventional manner to obtain the title compound (42 mg, yield 29%) as yellow powder.

$^1$H NMR (CD$_3$OD, 400 MHz) δ: 3.10 (2H, t, J=7 Hz), 3.42 (2H, t, J=7 Hz), 4.2-4.6 (2H, m), 7.37 (1H, d, J=8 Hz), 7.68 (2H, d, J=8 Hz), 7.8-7.9 (6H, m), 8.02 (1H, d, J=8 Hz), 8.09 (1H, d, J=8 Hz), 8.48 (2H, d, J=3 Hz), 8.73 (1H, d, J=8 Hz)

(2-b) N-[4-(2-Oxo-2,3-dihydro-1H-naphtho[1,2-e][1,4]-diazepin-5-yl)phenyl]-3-(pyridin-2-yl)propionamide dihydrochloride 5-(4-Aminophenyl)-1H-naphtho[1,2-e][1,4]diazepin-2(3H)-one (100 mg, 0.330 mmol) obtained above, and 3-(pyridin-2-yl)propionyl chloride (60.0 mg, 0.360 mmol) were stirred at 80° C. for 12 hours in a pyridine solvent. The solvent was evaporated, then saturated aqueous sodium hydrogencarbonate was added to the residue, and the resulting mixture was extracted with an organic solvent. The organic layer was washed with saturated brine, and dried over anhydrous sodium sulfate. The solvent was evaporated under reduced pressure, and the residue was purified by silica gel chromatography (methanol/chloroform=1/20) to obtain N-[4-(2-oxo-2,3-dihydro-1H-naphtho[1,2-e][1,4]-diazepin-5-yl)phenyl]3-(pyridin-2-yl)propionamide (58 mg) as yellow crystals. The crystals were dissolved in chloroform (30 mL) and methanol (30 mL), 4 M hydrogen chloride in ethyl acetate (0.13 mL) was added to the solution, and the solvent was evaporated under reduced pressure to obtain yellow crystals (58 mg), The crystals were refluxed in ethanol (6 mL) by heating for 6 hours, then collected by filtration, concentrated twice from water under reduced pressure, and dried under reduced pressure to obtain the title compound (40 mg, yield 24%) as yellow powder.

The NMR data are the same as those indicated in (2) mentioned above.

Example 2

2-Ethyl-3-hydroxy-N-[4-(2-oxo-2,3-dihydro-1H-naphtho[1,2-e][1,4]-diazepin-5-yl)phenyl]benzamide

(1) 2-Ethyl-3-methoxy-N-[4-(2-oxo-2,3-dihydro-1H-naphtho[1,2-e][1,4]-diazepin-5-yl)phenyl]benzamide By using 5-(4-aminophenyl)-1H-naphtho[1,2-e][1,4]diazepin-2(3H)-one (150 mg, 0.497 mmol) obtained in Example 1, (1), and 2-ethyl-3-methoxybenzoyl chloride (0.360 mmol), the title compound (90 mg, yield 39%) was obtained in the same manner as that of Example 1, (2).

(2) 2-Ethyl-3-hydroxy-N-[4-(2-oxo-2,3-dihydro-1H-naphtho[1,2-e][1,4]-diazepin-5-yl)phenyl]benzamide 2-Ethyl-3-methoxy-N-[4-(2-oxo-2,3-dihydro-1H-naphtho[1,4]-diazepin-5-yl)phenyl]benzamide (90 mg, 0.194 mmol) was dissolved in dry dichloromethane (10 mL), a 1 M solution of boron tribromide in dichloromethane (1 mL, 1.0 mmol) was added to the solution, and the mixture was stirred at room temperature for 24 hours, Post-treatments were performed in a conventional manner to obtain the title compound (46 mg, yield 52%) as yellow powder.

$^1$H NMR (DMSO-d$_6$, 400 MHz) δ: 1.11 (3H, t, J=7 Hz), 2.65 (2H, q, J=7 Hz), 3.79 (1H, d, J=10 Hz), 4.57 (1H, d, J=10 Hz), 6.8-6.9 (2H, m), 7.10 (1H, t, J=8 Hz), 7.32 (1H, d, J=8 Hz), 7.53 (2H, d, J=9 Hz) 7.6-7.8 (5H, m), 8.0-8.1 (1H, m), 8.3-8.4 (1H, m), 9.58 (1H, s), 10.51 (1H, s), 10.85 (1H, s)

Example 3

2-Ethyl-N-[4-(2-oxo-2,3-dihydro-1H-naphtho[1,2-e][1,4]-diazepin-5-yl)phenyl]nicotinamide dihydrochloride

(1) 2-Ethyl-N-[4-(2-oxo-2,3-dihydro-1H-naphtho[1,2-e][1,4]-diazepin-5-yl)phenyl]nicotinamide By using 5-(4-aminophenyl)-1H-naphtho[1,2-e][1,4]diazepin-2(3H)-one (100 mg, 0.331 mmol) obtained in Example 1, (1), and 2-ethylnicotinic acid chloride, the title compound (31 mg, yield 21%) was obtained in the same manner as that of Example 1, (2).

$^1$H NMR (DMSO-d$_6$, 400 MHz) δ: 1.24 (3H, t, J=8 Hz), 2.89 (2H, q, J=8 Hz), 3.80 (1H, d, J=10 Hz), 4.57 (1H, d, J=10 Hz), 7.3-7.4 (2H, m), 7.56 (2H, d, J=8 Hz), 7.7-7.9 (6H, m), 8.04 (1H, d, J=9 Hz), 8.38 (1H, d, J=9 Hz), 8.62 (1H, d, J=4 Hz), 10.72 (1H, br s), 10.86 (1H, br s)

(2) 2-Ethyl-N-[4-(2-oxo-2,3-dihydro-1H-naphtho[1,2-e][1,4]-diazepin-5-yl)phenyl]nicotinamide hydrochloride By converting 2-ethyl-N-[4-(2-oxo-2,3-dihydro-1H-naphtho[1,2-e][1,4]-diazepin-5-yl)phenyl]nicotinamide obtained above into hydrochloride in a conventional manner, the title compound was obtained as yellow powder.

$^1$H NMR (DMSO-d$_6$, 400 MHz) δ: 1.26 (3H, J=7 Hz), 2.96 (2H, q, T=7 Hz), 4.10 (1H, br s), 4.52 (1H, br s), 7.32 (1H, d, J=9 Hz), 7.5-7.6 (1H, m), 7.69 (2H, d, J=8 Hz), 7.7-7.9 (3H, in), 7.92 (2H, d, J=9 Hz), 8.08 (1H, d, 8.1-8.2 (1H, m), 8.46 (1H, d, J=8 Hz), 8.71 (1H, d, J=4 Hz), 11.06 (1H, s), 11.37 (1H, br s)

Example 4

2-Ethyl-6-hydroxy-N-[4-(2-oxo-2,3-dihydro-1H-naphtho[1,2-e][1,4]-diazepin-5-yl)phenyl]benzamide

(1) 2-Ethyl-6-methoxy-N-[4-(2-oxo-2,3-dihydro-1H-naphtho[1,2-e][1,4]-diazepin-5-yl)phenyl]benzamide By using 5-(4-aminophenyl)-1H-naphtho[1,2-e][1,4]diazepin-2(3H)-one (200 mg, 0.663 mmol) obtained in Example 1, (1), and 2-ethyl-6-methoxybenzoic acid chloride (0.995 mmol), the title compound (200 mg, yield 65%) was obtained in the same manner as that of Example 1, (2).

(2) 2-Ethyl-6-hydroxy-N-[4-(2-oxo-2,3-dihydro-1H-naphtho[1,2-e][1,4,]-diazepin-5-yl)phenyl]benzamide By using 2-ethyl-6-methoxy-N-[4-(2-oxo-2,3-dihydro-1H-naphtho[1,2-e][1,4]-diazepin-5-yl)phenyl]benzamide mentioned above, the title compound was obtained as yellow crystals (yield 66%) in the same manner as that of Example 2, (2).

$^1$H NMR (DMSO-d$_6$, 400 MHz) δ: 1.16 (3H, t, J=7 Hz), 2.56 (2H, q, J=7 Hz), 3.79 (1H, d, J=10 Hz), 4.56 (1H, d, J=10 Hz), 6.75 (2H, t, J=8 Hz), 7.16 (1H, t, J=8 Hz), 7.33 (1H, d, J=8 Hz), 7.52 (2H, d, J=8 Hz), 7.6-7.8 (5H, m), 8.0-8.1 (1H, m), 8.3-8.4 (1H, m), 9.70 (1H, br s), 10.49 (1H, br s), 10.85 (1H, br s)

Example 5

3-Ethyl-N-[4-(2-oxo-2,3-dihydro-1H-naphtho[1,2-e][1,4]-diazepin-5-yl)phenyl]picolinamide hydrochloride

(1) 3-Ethyl-N-[4-(2-oxo-2,3-dihydro-1H-naphtho[1,2-e][1,4]-diazepin-5-yl)phenyl]picolinamide By using 5-(4-aminophenyl)-1H-naphtho[1,2-e][1,4]diazepin-2(3H)-one (100 mg, 0.331 mmol) obtained in Example 1, (1), and 3-ethylpicolinic acid chloride (0.663 mmol), the title compound (24 mg yield 16%) was obtained in the same manner as that of Example 1, (2).

$^1$H NMR (DMSO-d$_6$, 400 MHz) δ: 1.22 (3H, t, J=7 Hz), 2.96 (2H, t, J=7 Hz), 3.80 (1H, d, J=10 Hz), 4.57 (1H, d, J=10 Hz), 7.33 (1H, d, J=8 Hz), 7.56 (2H, d, J=9 Hz), 7.6-7.7 (3H, m), 7.8-7.9 (3H, m), 8.04 (1H, d, J=6 Hz), 8.38 (1H, d, J=5 Hz), 8.56 (1H, d, J=4 Hz), 10.77 (1H, br s), 10.85 (1H, br s).

(2) 3-Ethyl-N-[4-(2-oxo-2,3-dihydro-1H-naphtho[1,2-e][1,4]-diazepin-5-yl)phenyl]picolinamide hydrochloride By converting 3-ethyl-N-[4-(2-oxo-2,3-dihydro-1H-naphtho[1,2-e][1,4]-diazepin-5-yl)phenyl]picolinamide obtained above into hydrochloride in a conventional manner, the title compound was obtained as yellow powder.

$^1$H NMR (DMSO-d$_6$, 400 MHz) δ: 1.21. (3H, t, J=7 Hz), 2.96 (2H, q, J=7 Hz), 4.10 (1H, br s), 4.51 (1H, br s), 7.34 (1H, d, J=9 Hz), 7.57 (1H, dd, J=5 Hz, 8 Hz), 7.66 (2H, d, J=9 Hz), 7.7-7.9 (4H, m), 8.03 (2 h, d, J=9 Hz), 8.08 (1H, d, J=8 Hz), 8.45 (1H, d, J=8 Hz), 8.56 (1H, dd, J=1 Hz, 4 Hz), 10.96 (1H, s), 11.35 (1H, br s)

Example 6

N-[4-(2-Oxo-2,3-dihydro-1H-naphtho[1,2-e][1,4]-diazepin-5-yl)phenyl]-2-(pyridin-2-yloxy)acetamide hydrochloride (1) N-[4-(2-Oxo-2,3-dihydro-1H-naphtho[1,2-e][1,4]-diazepin-5-yl)phenyl]-2-(pyridin-2-yloxy)acetamide hydrochloride 5-(4-Aminophenyl)-1H-naphtho[1,2-e][1,4]-diazepin-2(3H)-one (82 mg, 0.531 mmol) obtained in Example 1, (1), 2-(pyridyl-2-yloxy)acetic acid (47 mg, 0.314 mmol), HATU (302 mg, 0.795 mmol), diisopropylethylamine (138 mg, 1.06 mmol), and dimethylformamide (10 mL) were mixed, and the mixture was stirred at room temperature for 16 hours under a nitrogen atmosphere. To the reaction mixture, saturated aqueous sodium hydrogencarbonate was added, and the resulting mixture was extracted with ethyl acetate. Purification was performed in a conventional manner to obtain the title compound (25 mg, yield 21%) as white solid.

$^1$H NMR (DMSO-$d_6$, 400 MHz) δ: 3.76 (1H, d, J=10 Hz), 4.55 (1H, d, J=10 Hz), 4.95 (2H, s), 6.9-7.0 (2H, m), 7.29 (1H, d, J=9 Hz), 7.51 (2H, d, J=8 Hz), 7.6-7.7 (6H, m), 8.01 (1H, br s), 8.14 (1H, d, J=4 Hz), 8.39 (1H, br s), 10.34 (1H, br s), 10.83 (1H, br, s)

(2) N-[4-(2-Oxo-2,3-dihydro-1H-naphtho[1,2-e][1,4]-diazepin-5-yl)phenyl]-2-(pyridin-2-yloxy)acetamide hydrochloride By converting N-[4-(2-oxo-2,3-dihydro-1H-naphtho[1,2-e][1,4]-diazepin-5-yl)phenyl]-2-(pyridin-2-yloxy)acetamide obtained above into hydrochloride in a conventional manner, the title compound was obtained as yellow powder.

$^1$H NMR (DMSO-$d_6$, 400 MHz) δ: 4.96 (2H, s), 6.95 (1H, d, J=9 Hz), 7.00 (1H, dd, J=5 Hz, 8 Hz), 7.30 (1H, d, J=9 Hz), 7.5-7.9 (8H, m), 8.0-8.2 (2H, m), 8.4-8.5 (1H, m), 10.54 (1H, br s), 11.28 (1H, br s)

Example 7

2(2-Methoxyphenyl)-N-[4-(2-oxo-2,3-dihydro-1H-naphtho[1,2-e][1,4]-diazepin-5-yl)phenyl]acetamide 5-(4-Aminophenyl)-1H-naphtho[1,2-e][1,4]diazepin-2(3H)-one (151 mg, 0.5 mmol) obtained in Example 1, (1), 2-methoxyphenylacetic acid (100 mg, 0.6 mmol), HATU (228 mg, 0.6 mmol), diisopropylethylamine (0.1 mL, 0.6 mmol), and dry dimethylformamide (5 mL) were mixed, and the mixture was stirred at room temperature for 16 hours. To this reaction mixture, water was added, the resulting mixture was extracted with ethyl acetate, and then the organic layer was washed with saturated aqueous sodium hydrogencarbonate, and then with saturated brine, and dried over anhydrous sodium sulfate. The solvent was evaporated under reduced pressure, and the residue was washed with chloroform, and then with hexane to obtain the title compound (116 mg) as pale yellow crystals. The washing solution was concentrated under reduced pressure, and the residue was purified by silica gel column chromatography (chloroform/methanol=50/1) to obtain the title compound (63 mg) as white crystals (total 179 mg, yield 80%).

$^1$H NMR (DMSO-$d_6$, 400 MHz) δ: 3.66 (2H, s), 3.7-3.8 (4H, m), 4.54 (1H, d, J=10 Hz), 6.90 (1H, t, J=7 Hz), 6.98 (1H, d, J=8 Hz), 7.2-7.3 (3H, an), 7.49 (2H, d, J=8 Hz), 7.6-7.8 (5H, m), 8.01 (1H, d, J=6 Hz), 8.86 (1H, d, J=7 Hz), 10.26. (1H, s), 10.81 (1H, s)

Example 8

N-[4-(2-Oxo-2,3-dihydro-1H-naphtho[1,2-e][1,4] diazepin-5-yl)-phenyl]-3-(pyridin-3-yl)propionamide dihydrochloride By using 5-(4-aminophenyl)-1,3-dihydro-naphtho[1,2-e][1,4]diazepin-2-one (100 mg, 0.331 mol) obtained in Example 1, (1), and 3-(pyridin-3-yl)propionic acid (55 mg, 0.365 mmol), the title compound was obtained as yellow crystals in the same manner as that of Example 6.

$^1$H NMR (DMSO-$d_6$, 400 MHz) δ: 2.81 (2H, t, J=7 Hz), 3.08 (2H, t, J=7 Hz), 3.92 (1H, s), 4.51 (1H, s), 7.28 (1H, d, J=9 Hz), 7.55 (2H, d, J=9 Hz), 7.6-7.7 (6H, m), 8.05 (1H, d, J=8 Hz), 8.29 (1H, s), 8.40 (1H, d, J=8 Hz), 8.68 (1H, d, J=5 Hz), 8.77 (1H, s), 10.35 (1H, s), 11.07 (1H, s)

Example 9

N-[4-(2-Oxo-2,3-dihydro-1H-naphtho[1,2-e][1,4] diazepin-5-yl)phenyl]-3-phenylpropanamide By using 5(4-aminophenyl)-1,3-dihydro-naphtho[1,2-e][1,4]diazepin-2-one (100 mg, 0.331 mol) obtained in Example 1, (1), and 3-phenylpropionic acid (55 mg, 0.365 mmol), the title compound was obtained (yield 76%) as yellow crystals in the same manner as that of Example 6.

$^1$H NMR (DMSO-$d_6$, 400 MHz) δ: 2.65 (2H, t, J=8 Hz), 2.91 (2H, t, J=8 Hz), 3.76 (1H, d, J=10 Hz), 4.53 (1H, d, J=10 Hz), 7.1-7.3 (6H, m), 7.48 (2H, d, J=9 Hz), 7.6-7.8 (5H, m), 7.9-8.1 (1H, m), 8.35 (1H, d, J=9 Hz), 10.11 (1H, br s), 10.80 (1H, br s)

Example 10

N-[4-(2,4-Dioxo-3,4-dihydro-1H-naphtho[1,2-b][1,4]diazepin-5(2H)-yl)-phenyl]-3-(pyridin-3-yl)propionamide hydrochloride (1) tert-Butyl 4-(1-nitro-2-naphthylamino)phenylcarbamate 1-Nitro-2-naphthyl trifluoromethanesulfonate (20.26 g, 63.07 mmol), tert-butyl 4-aminophenylcarbamate (13.13 g, 63.07 mmol), triphenylphosphine (1.65 g, 6.31 mmol), tetrakis(triphenylphosphine)palladium(0) (3.64 g, 3.15 mmol), potassium carbonate (8.72 g, 63.07 mmol), and degassed dry toluene (600 mL) were mixed, and the mixture was refluxed by heating for 6 hours under a nitrogen atmosphere. The reaction mixture was left to cool, and then the insoluble matter was separated by filtration, and washed with ethyl acetate. The organic layer was washed with saturated aqueous sodium hydrogencarbonate, and dried over anhydrous sodium sulfate. The solvent was evaporated under reduced pressure, and the residue was purified by silica gel column chromatography (hexane/ethyl acetate=4/1), and then recrystallized from ethyl acetate and hexane to obtain the title compound (18.67 g, yield 78%) as yellow crystals.

$^1$H NMR (CDCl$_3$, 400 MHz) δ: 1.54 (9H, s), 6.53 (1H, s), 7.21 (2H, d, J=9 Hz), 7.21 (1H, d, J=9 Hz), 7.37 (1H, t, J=7 Hz), 7.44 (2H, d, J=9 Hz), 7.62 (1H, dt, J=1 Hz, 9 Hz), 7.68 (1H, d, J=7 Hz), 7.70 (1H, d, J=9 Hz), 8.61 (1H, d, J=9 Hz), 9.67 (1H, s)

(2) tert-Butyl 4-(1-amino-2-naphthylamino)phenylcarbamate tert-Butyl 4-(1-nitro-2-naphthylamino)phenylcarbamate (18.67 g, 49.21 mmol) was dissolved in tetrahydrofuran (180 mL) and methanol (180 mL), platinum oxide (360 mg) was added to the solution, and the mixture was stirred at room temperature for 2 hours under a hydrogen atmosphere. The catalyst was separated by filtration, then the solvent was evaporated under reduced pressure, and the residue was washed with methanol to obtain the title compound (15.67 g, yield 91%) as grayish white crystals.

$^1$H NMR (DMSO-$d_6$, 400 MHz) δ: 1.45 (9H, s), 5.25 (2H, br s), 6.62 (2H, d, J=9 Hz), 7.0-7.3 (5H, m), 7.3-7.4 (2H, m), 7.72 (1H, d, J=8 Hz), 8.06 (1H, d, J=8 Hz), 8.90 (1H, br s)

(3) 5-(4-Aminophenyl)-1H-naphtho[1,2-b][1,4]-diazepine-2,4(3H, 5H)-dione tert-Butyl 4-(1-amino-2-naphthylamino)phenylcarbamate (3.00 g, 8.58 mmol), and sodium hydrogencarbonate (2.16 g, 25.7 mmol) were suspended in chloroform (60 mL), ethyl malonyl chloride (1.22 mL, 9.5 mmol) was added dropwise to the suspension over 1 minute with stirring under ice cooling. This reaction mixture was stirred for 1 hour under ice cooling, then water was added to the mixture, the resulting mixture was stirred for 10 minutes, and the chloroform layer was dried over anhydrous sodium sulfate. The solvent was evaporated under reduced pressure to obtain a crude product of ethyl 3-[[2-[[4-[(tert-butoxycarbonyl)amino]phenyl]amino]-1-naphthyl]amino]-3-oxopropionate (4 g) as brown crystals.

This crude product (4 g) was dissolved in dry tetrahydrofuran (172 mL), 60% sodium hydride (1.72 g, 42.9 mmol) was added to the solution over 1 minute with stirring under ice cooling, and the mixture was stirred under ice cooling for 30 minutes, and then at room temperature for 3 hours. To this reaction mixture, saturated aqueous ammonium chloride was added with stirring under ice cooling, and the organic layer was dried over anhydrous sodium sulfate. The solvent was evaporated under reduced pressure to obtain a crude product of 5-(4-tert-butoxycarbonylaminophenyl)-1H-naphtho[1,2-b][1,4]diazepine-2,4(3H,5H)-dione (4 g) as pale brown crystals.

This crude product (4 g) was suspended in dichloromethane (176 mL), trifluoroacetic acid (13.1 mL, 176 mL) was added dropwise to the suspension over 10 minutes with stirring under ice cooling, and the mixture was stirred under ice cooling for 1 hour, and then at room temperature for 16 hours. The solvent was evaporated at room temperature, saturated aqueous sodium hydrogencarbonate and ethyl acetate were added to the residue, and the mixture was stirred at room temperature for 2 hours. The deposited crystals were collected by filtration, and washed with water and then with ethyl acetate to obtain the title compound (1.23 g, yield 45%) as brown crystals.

$^1$H NMR (DMSO-$d_6$, 400 MHz) δ: 3.10 (1H, d, J=12 Hz), 3.61 (1H, d, J=12 Hz), 5.26 (2H, s), 6.58 (2H, d, J=91 Hz), 6.84 (2H, d, J=8 Hz), 7.04 (1H, d, J=9 Hz), 7.57 (1H, t, J=7 Hz), 7.6-7.7 (2H, m), 7.90 (1H, d, j=8 Hz), 8.22 (1H, 4, J=8 Hz), 10.80 (1H, s)

(4) N-[4-(2,4-Dioxo-3,4-dihydro-1H-naphtho[1,2-b][1,4]diazepin-5(2H)-yl)-phenyl]-3-(pyridin-3-yl)propionamide hydrochloride By using 5-(4-aminophenyl)-1,5-dihydronaphtho[1,2-b][1,4]diazepine-2,4-dione (50 mg, 0.157 mol) obtained above, and 3-(pyridin-3-yl)propionic acid (26 mg, 0.173 mmol), the title compound was obtained as a slightly brown amorphous substance in the same manner as that of Example 6.

$^1$H NMR (DMSO-$d_6$, 400 MHz) δ: 2.80 (2H, t, J=7 Hz), 3.11 (2H, t, J=7 Hz), 3.16 (1H, d, J=12 Hz), 3.69 (1H, d, J=12 Hz), 6.97 (1H, d, J=9 Hz), 7.15 (2H, d, J=9 Hz), 7.6-7.7 (5H, m), 7.9-8.0 (2H, m), 8.25 (1H, d, J=8 Hz), 8.43 (1H, d, J=8 Hz), 8.73 (1H, d, J=5 Hz), 8.84 (1H, s), 10.24 (1H, s), 10.89 (1H, s)

Example 11

N-[4-(2,4-Dioxo-3,4-dihydro-1H-naphtho[1,2-b][1,4]diazepin-5(2H)-yl)-phenyl]-3-(pyridin-4-yl)propionamide hydrochloride By using 5-(4-aminophenyl)-1,5-dihydronaphtho[1,2-b][1,4]diazepine-2,4-dione (30 mg, 0.0945 mol) obtained in Example 10, (3), and 3-(pyridin-4-yl)propionic acid (16 mg, 0.103 mmol), the title compound was obtained as a pale yellow amorphous substance in the same manner as that of Example 6.

$^1$H NMR (DMSO-$d_6$, 400 MHz) δ: 2.83 (2H, t, j=7 Hz), 3.15 (2H, t, J=7 Hz), 3.3-3.4 (1H, m), 3.70 (1H, d, J=12 Hz), 6.98 (1H, dd, j=9 Hz), 7.16 (2H, dd, J=3, 9 Hz), 7.6-7.7 (5H, m), 7.83 (2H, s), 7.91 (1H, s), 8.25 (1H, d, J=5 Hz), 8.74 (2H, d, j=5 Hz), 10.19 (1H, s), 10.89 (1H, s)

Example 12

2-tert-Butyl-N-[4-(2,4-dioxo-3,4-dihydro-1H-naphtho[2,1-b][1,4]diazepin-5(2H)-yl)2-fluorophenyl]benzamide 5-(4-Amino-3-fluorophenyl)-1H-naphtho[2,1-b][1,4]diazepin-2,4(3H,5H)-dione (35 mg, 0.104 mmol) synthesized by using 1-nitro-2-naphthyl trifluoromethanesulfonate, and tert-butyl 4-amino-2-fluorophenylcarbamate in the same manner as that of Example 10, (1), (2), and (3), dry pyridine (3 mL), and 2-tert-butylbenzoyl chloride (62.9 mg, 0.320 mmol) were mixed, and the mixture was stirred at room temperature for 4.5 hours. To the reaction mixture, saturated aqueous sodium hydrogencarbonate was added, the resulting mixture was extracted with chloroform, and the organic layer was washed with saturated brine, and dried over anhydrous sodium sulfate. The solvent was evaporated under reduced pressure, and the residue was purified by silica gel chromatography to obtain the title compound (26 mg, yield 49%) as white crystals.

$^1$H NMR (CDCl$_3$, 400 MHz) δ: 1.46 (9H, s), 3.61. (2H, s), 7.0-7.1 (2H, m), 7.18 (1H, dd, J=2, 12 Hz), 7.35 (1H, d, J=6 Hz), 7.41 (1H, t, J=8 Hz), 7.55 (1H, d, J=7 Hz), 7.6-7.7 (3H, m), 7.71 (1H, t, J=7 Hz), 7.88 (1H, d, J=8 Hz), 8.32 (1H, br s), 8.54 (1H, t, J=9 Hz)

Example 13

N-[4-(2,4-Dioxo-3,4-dihydro-1H-naphtho[1,2-b][1,4]diazepin-5(2H)-yl)-phenyl]-3-(pyridin-2-yl)propionamide hydrochloride By using 5-(4-aminophenyl)-1,5-dihydronaphtho[1,2-b][1,4]diazepine-2,4-dione (100 mg, 0.315 mol) obtained in Example 10, (3), and 3-(pyridin-2-yl) propionic acid chloride (0.472 mmol), the title compound was obtained as slightly brown solid in the same manner as that of Example 3.

$^1$H NMR (DMSO-d$_6$, 400 MHz) δ: 3.02 (2H, t, J=7 Hz), 3.14 (1H, d, J=12 Hz), 3.36 (2H, t, J=7 Hz), 3.69 (1H, d, J=12 Hz), 6.97 (1H, d, J=9 Hz), 7.15 (2H, d, J=8 Hz), 7.5-7.7 (5H, m), 7.8-7.9 (2H, m), 8.01 (1H, d, J=8 Hz), 8.25 (1H, d, J=9 Hz), 8.49 (1H, d, J=8 Hz), 8.80 (1H, d, J=6 Hz), 10.55 (1H, br s), 10.92 (1H, br s)

Example 14

2-(Dimethylamino)-N-[4-(2,4-dioxo-2,3-dihydro-1H-naphtho[1,2-b][1,4]diazepin-5(2H)-yl)phenyl]nicotinamide hydrochloride By using 5-(4-aminophenyl)-1H-naphtho[1,2-b][1,4]diazepine-2,4(3H,5H)-dione (63 mg, 0.2 mmol)) obtained in Example 10, (3), and 2-(dimethylamino)nicotinic acid (49 mg, 0.24 mmol), the title compound (55 mg, yield 55%) was obtained as slightly yellow crystals in the same manner as that of Example 6.

$^1$H NMR (DMSO-d$_6$, 400 MHz) δ: 3.02 (6H, s), 3.16 (1H, d, J=12 Hz), 3.71 (1H, d, J=12 Hz), 6.82 (1H, dd, J=5 Hz, 7 Hz), 7.02 (1H, d, J=9 Hz), 7.22 (2H, d, J=9 Hz), 7.60 (1H, t, J=7 Hz), 7.6-7.9 (5H, m), 7.92 (1H, d, J=8 Hz), 8.20 (1H, dd, J=1 Hz 5 Hz), 8.26 (1H, d, J=8 Hz), 10.61 (1H, s), 10.90 (1H, s)

Example 15

2-(Dimethylamino)-N-[4-(2-oxo-2,3-dihydro-1H-naphtho[1,2-e][1,4]diazepin-5-yl)phenyl]nicotinamide dihydrochloride By using 5-(4-aminophenyl)-1H-naphtho[1,2-e][1,4]diazepin-2(3H)-one (60 mg, 0.2 mmol) obtained in Example 1, (1), and 2-(dimethylamino)nicotinic acid (61 mg, 0.3 mmol), the title compound (23 mg, yield 22%) was obtained as yellow crystals in the same manner as that of Example 6.

$^1$H NMR (DMSO-d$_6$, 400 MHz) δ: 3.04 (6H, s), 4.0-4.2 (1H, m), 4.4-4.6 (1H, m), 6.86 (1H, t, J=6 Hz), 7.33 (1H, d, J=9 Hz), 7.67 (2H, d, J=9 Hz), 7.7-7.9 (6H, m), 8.08 (1H, d, J=7 Hz), 8.22 (1H, d, J=5 Hz), 8.46 (1H, d, J=8 Hz), 10.92 (1H, s), 11.33 (1H, br s)

Example 16

2-(Dimethylamino)-N-[4-(2-oxo-2,3-dihydro-1H-naphtho[1,2-e][1,4]diazepin-5-yl)phenyl]nicotinamide dihydrochloride (1) 2-Chloro-N-[4-(2-oxo-2,3-dihydro-1H-naphtho[1,2-e][1,4]diazepin-5-yl)phenyl]nicotinamide 5-(4-Aminophenyl)-1H-naphtho[1,2-e][1,4]diazepin-2(3H)-one (45.2 g, 150 mmol) obtained in Example 1, (1) was suspended in dry tetrahydrofuran (1500 mL), and triethylamine (41.9 mL, 300 mmol) was added to the suspension. To this mixture, 2-chloronicotinic acid chloride (29.0 g, 165 mmol) was added dropwise over 5 minutes, and the resulting mixture was stirred at room temperature for 1 hour, and then refluxed by heating for 8 hours. The reaction mixture was cooled to room temperature, then water (500 mL) and ethyl acetate (500 mL) were added to the mixture, and the resulting mixture was stirred at room temperature for 1 hour. The organic layer was washed with saturated aqueous sodium hydrogencarbonate, and then with saturated brine, and dried over anhydrous sodium sulfate. The solvent was evaporated under reduced pressure, and the residue was concentrated from ethyl acetate, and then washed with ethyl acetate, and then with hexane to obtain the title compound (54.7 g) as pale yellow crystals. The washing solution was concentrated under reduced pressure, and the residue was purified by silica gel column chromatography (chloroform/methanol=20/1), and washed with ethyl acetate, and then with hexane to obtain the title compound (3.7 g) as slightly brown crystals (total 58.4 g, yield 88%).

$^1$H NMR (DMSO-d$_6$, 400 MHz) δ: 3.80 (1H, d, J=10 Hz), 4.57 (1H, d, J=10 Hz), 7.31 (1H, d, J=9 Hz), 7.5-7.6 (3H, m), 7.6-7.8 (5H, m), 8.0-8.1 (1H, m), 8.11 (1H, dd, J=2 Hz, 8 Hz), 8.3-8.4 (1H, m), 8.55 (1H, dd, J=2 Hz, 5 Hz), 10.83 (1H, s), 10.86 (1H, s)

(2) 2-(Dimethylamino)-N-[4-(2-oxo-2,3-dihydro-1H-naphtho[1,2-e][1,4]diazepin-5-yl)phenyl]nicotinamide 2-Chloro-N-[4-(2-oxo-2,3-dihydro-1H-naphtho[1,2-e][1,4]diazepin-5-yl)phenyl]nicotinamide (0.41 g, 0.93 mmol), ethanol (14 mL), and a 2 M solution of dimethylamine in ethanol (14 mL) were mixed, and the mixture was refluxed by heating for 18 hours. The reaction mixture was cooled to room temperature, and then the crystals were collected by filtration, and washed with ethanol to obtain the title compound (0.35 g, yield 71%) as slightly yellow crystals.

$^1$H NMR (DMSO-d$_6$, 400 MHz) δ: 3.79 (1H, d, J=10 Hz), 4.56 (1H, d, J=10 Hz), 6.76 (1H, dd, J=5 Hz, 8 Hz), 7.32 (1H, d, J=9 Hz), 7.54 (2H, d, J=9 Hz), 7.6-7.8 (6H, m), 8.0-8.1 (1H, m), 8.21 (1H, dd, J=2 Hz, 5 Hz), 8.3-8.4 (1H, m), 10.58 (1H, s), 10.82 (1H, s)

(3) 2-(Dimethylamino)-N-[4-(2-oxo-2,3-dihydro-1H-naphtho[1,2-e][1,4]diazepin-5-yl)phenyl]nicotinamide dihydrochloride 2-(Dimethylamino)-N-[4-(2-oxo-2,3-dihydro-1H-naphtho[1,2-e][1,4]diazepin-5-yl)phenyl]nicotinamide (32.8 g, 73 mmol) was suspended in ethanol (660 mL), 2 M hydrochloric acid (80 mL) was added to the suspension, and the mixture was stirred at room temperature for 65 hours. The crystals were collected by filtration, washed with ethanol, air-dried overnight, and then dried at 80° C. for 3 days under reduced pressure to obtain the title compound (30.2 g, yield 79%) as yellow crystals.

The NMR data were the same as those mentioned in Example 15.

Example 17

2-(Dimethylamino)-N-[4-(2-oxo-2,3-dihydro-1H-naphtho[1,2-e][1,4]diazepin-5-yl)phenyl]nicotinamide dimethanesulfonate 2-(Dimethylamino)-N-[4-(2-oxo-2,3-dihydro-1H-naphtho[1,2-e][1,4]diazepin-5-yl)phenyl]nicotinamide (376 mg, 0.84 mmol) obtained in Example 16, (2), and methanesulfonic acid (161 mg, 1.68 mmol) were dissolved in water (0.8 mL) and ethanol (0.8 mL), ethanol (8 mL) was added to the solution, and the mixture was stirred at room temperature for 2 hours. The deposited crystals were collected by filtration, and washed with ethanol to obtain the title compound (445 mg, yield 82%) as yellow crystals.

¹H NMR (DMSO-d₆, 400 MHz) δ: 2.32 (6H, s), 3.04 (6H, s), 4.0-4.2 (1H, in), 4.4-4.6 (1H, m), 6.87 (1H, dd, J=5 Hz, 7 Hz), 7.33 (1H, d, J=9 Hz), 7.66 (2H, d, J=9 Hz), 7.7-7.9 (4H, m), 7.89 (2H, d, J=9 Hz), 8.09 (1H, d, J=8 Hz), 8.22 dd, J=2H), 8.46 (1H, d, J=8 Hz), 10.89 (1H, s), 11.35 (1H, bs)

Example 18

N-[4-(2,4-Dioxo-3,4-dihydro-1H-naphtho[1,2-b][1,4]-diazepin-5(2H)-yl)phenyl]-2-(morpholin-4-yl)-nicotinamide hydrochloride To a solution of 2-(morpholin-4-yl)nicotinic acid (63.5 mg, 0.315 mmol) anhydrous dimethylformamide (5 mL), HATU (144 mg, 0.378 mmol), and diisopropylethylamine (48.0 mg, 0.378 mmol) were added. The mixture was stirred at room temperature for 30 minutes under a nitrogen atmosphere, then 5-(4-aminophenyl)-1H-naphtho[1,2-b][1,4]diazepine-2,4(3H,5H)-dione (100 mg, 0.315 mmol) obtained in Example 10, (3) was added to the mixture, and the resulting mixture was stirred at room temperature for 16 hours under a nitrogen atmosphere. The reaction mixture was treated in the same manner as that of Example 7 to purify the product, and the product was made into hydrochloride in a conventional manner to obtain the title compound as yellow powder (yield 42%).
¹H NMR (CD₃OD, 400 MHz) δ: 3.34 (1H, d, J=1.2 Hz), 3.53 (4H, t, J=5 Hz), 3.70 (1H, d, J=12 Hz), 3.80 (4H, t, J=5 Hz), 7.06 (1H, d, J=9 Hz), 7.21 (1H, dd, J=7 Hz), 7.2-7.3 m), 7.5-7.6 m), 7.6-7.7 (2H, m), 7.7-7.8 (2H, m), 7.88 (1H, d, J=8 Hz), 8.1-8.3 (2H, m), 8.26 (1H, dd, J=7 Hz J=2 Hz)

Example 19

N-[4-(2-Oxo-2,3-dihydro-1H-naphtho[1,2-e][1,4]-diazepin-5-yl)phenyl]-2-(1H-pyrrol-1-yl)nicotinamide dihydrochloride To a solution of 2-(1H-pyrrol-1-yl)nicotinic acid hydrochloride (337 mg, 1.50 mmol) in anhydrous dimethylformamide (10 mL), HATU (860 mg, 2.25 mmol), and diisopropylethylamine (585 mg, 4.50 mmol) were added. The mixture was stirred at room temperature for 30 minutes under a nitrogen atmosphere, then 5-(4-aminophenyl)-1H-naphtho[1,2-e][1,4]diazepin-2(3H)-one (150 mg, 0.50 mmol) obtained in Example 1, (1) was added to the mixture, and the resulting mixture was stirred for 16 hours under a nitrogen atmosphere. The reaction mixture was treated in the same manner as that of Example 7 to purify the product, and the product was made into hydrochloride in a conventional manner to obtain the title compound as yellow powder (yield 26%).
¹H NMR (DMSO-d₆, 400 MHz) δ: 4.1-4.3 (1H, m), 4.4-4.6 (1H, m), 6.24 (2H, t, J=2 Hz), 7.28 (2H, t, J=2 Hz), 7.33 (1H, d, J=9 Hz), 7.49 (1H, dd, J=8 Hz, J=5 Hz), 7.6-7.9 (7H, m), 8.0-8.2 (2H, m), 8.48 (1H, d, J=8 Hz), 8.63 (1H, dd, J=5 Hz, J=2 Hz), 11.18 (1H, brs), 11.57 (1H, brs)

Example 20

2-(Morpholin-4-yl)-N-[4-(2-oxo-2,3-dihydro-1H-naphtho[1,2-e][1,4]-diazepin-5-yl)phenyl]nicotinamide dihydrochloride To a solution of 2-(morpholin-4-yl) nicotinic acid (208 mg, 1.00 mmol) in anhydrous dimethylformamide (3 mL). HATU (573 mg, 1.50 mmol), and diisopropylethylamine (387 mg, 3.00 mmol) were added. The mixture was stirred at room temperature for 30 minutes under a nitrogen atmosphere, then 5-(4-aminophenyl)-1H-naphtho[1,2-e][1,4]diazepin-2(3H)-one (100 mg, 0.33 mmol) obtained in Example 1, (1) was added to the mixture, and the resulting mixture was stirred at room temperature for 16 hours under a nitrogen atmosphere. The reaction mixture was treated in the same manner as that of Example 7 to purify the product, and the product was made into hydrochloride in a conventional manner to obtain the title compound as yellow powder (yield 32%).
¹H NMR (DMSO-d₆, 400 MHz) δ: 3.30 (4H, t, J=5 Hz), 3.6-3.7 (4H, m), 4.1-4.3 (1H, m), 4.4-4.7 (2H, m), 7.03 (1H, dd, J=8 Hz, J=5 Hz), 7.34 (1H, d, J=9 Hz), 7.71 (2H, d, J=8 Hz), 7.7-8.0 (4H, m), 7.96 (2H, d, J=8 Hz), 8.10 (1H, d, J=7 Hz), 8.35 (1H, dd, J=5 Hz, J=2 Hz), 8.48 (1H, d, J=8 Hz), 10.97 (1H, brs), 11.49 (1H, brs)

Example 21

N-[4-(2-Oxo-2,3-dihydro-1H-naphtho[1,2-e][1,4]-diazepin-5-yl)phenyl]-2-(pyrrolidin-1-yl)nicotinamide dihydrochloride To a solution of 2-(pyrrolidin-1-yl)nicotinic acid sodium salt (214 mg, 1.00 mmol) in anhydrous dimethylformamide (10 mL), HATU (420 mg, 1.10 mmol), and diisopropylethylamine (193 mg, 1.50 mmol) were added. The mixture was stirred at room temperature for 30 minutes under a nitrogen atmosphere, then 5-(4-aminophenyl)-1H-naphtho[1,2-e][1,4]diazepin-2-(3H)-one (200 mg, 0.67 mmol) obtained in Example 1, (1) was added to the mixture, and the resulting mixture was stirred at 80° C. for 16 hours under a nitrogen atmosphere. The reaction mixture was treated in the same manner as that of Example 7 to purify the product, and the product was made into hydrochloride in a conventional manner to obtain the title compound as yellow powder (yield 12%).
¹H NMR (DMSO-d₆, 400 MHz) δ: 1.9-2.1 (4H, m), 3.6-3.8 (4H, m), 4.1-4.3 (1H, m), 4.4-4.6 (1H, m), 6.99 (1H, t, J=7 Hz), 7.33 (1H, d, J=9 Hz), 7.7-7.9 (5H, m), 7.95 (2H, d, J=9 Hz), 8.11 (1H, d, J=8 Hz) 8.1-8.3 (2H, m), 8.49 (1H, d, J=8 Hz), 11.4 (1H, brs), 11.5 (1H, brs)

Example 22

4-(Dimethylamino)-N-[4-(2-oxo-2,3-dihydro-1H-naphtho[1,2-e][1,4]diazepin-5 yl)phenyl]nicotinamide dihydrochloride To a solution of 4-(dimethylamino)nicotinic acid potassium salt (100 mg, 0.49 mmol) in anhydrous dimethylformamide (10 mL), HATU (281 mg, 0.735 mmol), and diisopropylethylamine (190 mg, 1.47 mmol) were added under ice cooling. The mixture was stirred at room temperature for 3 hours under a nitrogen atmosphere, then 5-(4-aminophenyl)-1H-naphtho[1,2-e][1,4]diazepin-2(3H)-one (40 mg, 0.133 mmol) obtained in Example 1, (1) was added to the mixture, and the resulting mixture was stirred at 35° C. for 16 hours under a nitrogen atmosphere. The reaction mixture was treated in the same manner as that of Example 7 to purify the product, and the product was made into hydrochloride in the same manner as that of Example 16, (3) to obtain the title compound as yellow powder (yield 14%).
¹H NMR (DMSO-d₆, 400 MHz) δ: 3.19 (6H, s), 4.1-4.3 (1H, m), 4.4-4.6 (1H, m), 7.19 (1H, d, J=8 Hz), 7.31 (1H, d, J=9 Hz), 7.7-7.9 (5H, m), 7.99 (2H, d, J=9 Hz), 8.10 (1H, d, J=8 Hz), 8.30 (1H, d, J=8 Hz), 8.49 (1H, d, J=8 Hz), 8.61 (1H, s), 11.6 (1H, brs), 11.7 (1H, brs)

Example 23

2-Isopropyl-N-[4-(2-oxo-2,3-dihydro-1H-naphtho[1,2-e][1,4]diazepin-5 yl)phenyl]nicotinamide dihydrochloride To a solution of 2-isopropylnicotinic acid hydrochloride (350 mg, 1.70 mmol) in anhydrous dimethylformamide (20 mL), HATU (990 mg, 2.60 mmol), and diisopropylethylamine (700 mg, 5.40 mmol) were added. The mixture was stirred for 2 hours under a nitrogen atmosphere, then 5-(4-aminophenyl)-1H-naphtho[1,2-e][1,4]diazepin-2(3H)-one (170 mg, 0.570 mmol) obtained in Example 1, (1) was added to the mixture, and the resulting mixture was stirred at 80° C. for 16 hours under a nitrogen atmosphere. The reaction mixture was treated in the same manner as that of Example 7 to purify the product, and the product was made into hydrochloride in the same manner as that of Example 16, (3) to obtain the title compound (yield 10%) as yellow powder.

$^1$H NMR (CD$_3$OD, 400 MHz) δ: 1.54 (6H, d, J=7 Hz), 3.76 (1H, q, J=7 Hz), 4.56 (2H, brs), 7.44 (1H, d, J=9 Hz), 7.7-8.0 (5H, m), 8.0-8.2 (4H, m), 8.53 (1H, d, J=8 Hz), 8.80 (1H, dd, J=8 Hz, J=1 Hz), 8.91 (1H, dd, J=6 Hz, J=1 Hz)

Example 24

2-(Isopropylamino)-N-[4-(2-oxo-2,3-dihydro-1H-naphtho[1,2-e][1,4]diazepin-5-yl)phenyl]nicotinamide dihydrochloride To a solution of 2-(isopropylamino)nicotinic acid (400 mg, 2.22 mmol) in anhydrous dimethylformamide (10 mL), HATU (1.00 g, 2.62 mmol), and diisopropylethylamine (860 mg, 6.66 mmol) were added. The mixture was stirred for 2 hours under a nitrogen atmosphere, then 5-(4-aminophenyl)-1H-naphtho[1,2-e][1,4]diazepin-2(3H)-one (150 mg, 0.50 mmol) obtained in Example 1, (1) was added to the mixture, and under a nitrogen atmosphere, the resulting mixture was stirred at 30° C. for 10 hours, and then further stirred at 90° C. for 3 hours. The reaction mixture was treated in the same manner as that of Example 7 to purify the product, and the product was made into hydrochloride in the same manner as that of Example 16, (3) to obtain the title compound (yield 21%) as yellow powder.

$^1$H NMR (CD$_3$OD, 400 MHz) δ: 1.41 (6H, d, J=6 Hz), 4.0-4.1 (1H, m), 4.1-4.7 (2H, m), 7.0-7.1 (1H, m), 7.41 (1H, d, J=8 Hz), 7.7-7.9 (5H, m), 8.10 (4H, dd, J=7 Hz), 8.50 (1H, d, J=7 Hz), 8.68 (1H, d, J=6 Hz)

Example 25

(P2X4 Receptor Antagonist Activity)
(Test Method)

The P2X4 receptor antagonist activities of the compounds of the present invention were measured as follows.

The 1321N1 cells stably expressing human P2X4 receptor were seeded on a 96-well plate, cultured under the conditions of 37° C. and 5% CO$_2$ for 24 hours, and then used for intracellular calcium measurement. Fura-2 AM, which is a calcium fluorescent indicator, was used for the intracellular calcium measurement, Fura-2 AM dissolved in an assay buffer was added to the cells, the cells were left standing at room temperature for 45 minutes so that Fura-2 AM was incorporated into the cells, and then the plate was used for the fluorescence measurement. The treatment of the cells with each test substance was performed 15 minutes before the addition of ATP, and inflow of calcium into the cells as a response induced by the addition of ATP was measured over time by using a microplate reader. The ratio of fluorescence values obtained, with excitation lights of 340 nm and 380 nm was used as an index of the change of intracellular calcium level, and the inhibitory activity of the test substance was calculated on the basis of the comparison with the value obtained in the absence of the test substance (control).
(Test Results)

TABLE 9

| Test compound | Inhibitory activity IC$_{50}$ (μM) |
|---|---|
| Example 2 | 0.77 |
| Example 3 | 1.6 |
| Example 4 | 1.5 |
| Example 7 | 0.97 |
| Example 12 | 0.37 |
| Example 14 | 0.59 |
| Paroxetine | 4.0 |

As clearly seen from the results shown in Table 9, it was found that the compounds of the present invention have superior P2X4 receptor antagonist activity.

Example 26

(P2X4 Receptor Antagonist Activity)
(Test Method)

In the same manner as that of Example 26, the P2X4 receptor antagonist activities were measured. The results are shown in Table 10.
(Test Results)

TABLE 10

| Test compound | Inhibitory activity IC$_{50}$ (μM) |
|---|---|
| Example 15 | 0.88 |
| Example 18 | 1.3 |
| Example 19 | 2.4 |
| Example 20 | 2.5 |
| Example 21 | 1.3 |
| Example 22 | 1.5 |
| Example 23 | 2.3 |
| Example 24 | 8.6 |
| Paroxetine | 4.0 |

As clearly seen from the results shown in Table 10, it was found that the compounds of the present invention described in the examples have superior P2X4 receptor antagonist activity.

Example 27

(P2X Receptor Family Selectivity of the Compound Described in Example 15)
(Test Method)

Inhibitory activities of the compound described in Example 15 against the P2X3 receptor and P2X7 receptor, among the P2X receptor family members, were evaluated by the calcium imaging method using cells expressing each receptor, and compared with the inhibitory activity against the human P2X4 receptor. The inhibitory activities of the compound against the rat and mouse P2X4 receptors were also confirmed.

TABLE 11

| Receptor | Inhibition of agonist-induced Ca$^{2+}$ influx (IC$_{50}$, μM) |
| --- | --- |
| Human P2X4 | 0.88 |
| Mouse P2X4 | 0.52 |
| Rat P2X4 | 1.3 |
| Rat P2X3 | 6.8 |
| Rat P2X7 | >30 |
| Human P2X7 | >30 |

As shown in Table 11, the compound described in Example 15 showed high selectivity for the P2X4 receptor. Species-specific difference of the P2X4 receptor inhibitory activity was not observed among human, mouse, and rat.

Example 28

(Analgesic Activity)

The analgesic activity of the compound of the present invention was measured by the following method.

Preparation of Rat Neuropathic Pain Model (Modified Chung Model)

Rat neuropathic pain model (modified Chung model) was prepared according to the method of Kim, S. H., Chung, J. M. et al. (An experimental model for peripheral neuropathy produced by segmental spinal nerve ligation in the rat, Pain, 50, 355-363 (1992)). More specifically; under isoflurane anesthesia, back hair of rats was extensively shaved, the shaved parts were wiped with rubbing alcohol, the rats were fixed in the prone position on a heating pad, and the skins were cut and opened along the dorsal median line on the upper and lower sides of the sacroiliac bone. The left lateral paravertebral muscle was separated in the sacral region, and then the ligament was separated. The sacroiliac rim and the upper part thereof were cut and opened along the pyramid, the L5 spinal nerve was ligated, and the nerve was cut on the peripheral side. Then, the operative wound was sutured.

Measurement of Pain Threshold and Calculation Method of 50% Threshold

The pain threshold (paw withdrawal threshold (g)) was measured by stimulating the soles of rats with each of seven von Frey filaments (Stoelting Co., TOUCH-TEST SENSORY EVALUATOR) that gave different stimulation strengths, and determining presence or absence of withdrawal response. The 50% threshold was calculated according to the up down method with reference to the method of Chaplan et al. (Chaplan S R, Bach F W, Pogrel J W, Chung J M, Yaksh T L: Quantitative assessment of tactile allodynia in the rat paw, J. Neurosci. Method, 53:55-63 (1994)).

Evaluation Method and Results

For evaluation of efficacy, the compound described in Example 15 was repeatedly orally administered to the rats with a sonde for oral administration in rats for 14 days from the day 9 after the modified Chung operation, and effect thereof on the pain threshold measured in the von Frey filament test was observed. As a result, pain threshold of the affected limb was increased by 14 days-repeated oral administration of 30 mg/kg of the compounds described in Example 15 twice a day (60 mg/kg/day), and significant statistical difference between the vehicle group and the compound administration group was found (FIG. 1), The pain thresh old was measured 3 hours after the administration.

In FIG. 1:

Mean±S.E.M. (n=X·Y), ***; P<0.001 (60 mg/kg/day), *; P<0.05 (60 mg/kg/day) vs. vehicle group.

Two-Way ANOVA Boneferroni post tests

EXPLANATION OF SYMBOLS

In FIG. 1, the open circles (○) indicate the results obtained with administration of the vehicle (n=7 to 10), and the black solid circles (●) indicate the results obtained with administration of 60 mg/kg/day of the compound described in Example 15 (n=5 to 10).

The invention claimed is:

1. A compound of the following formula (I), a tautomer or a stereoisomer of the compound, or a pharmacologically acceptable salt thereof:

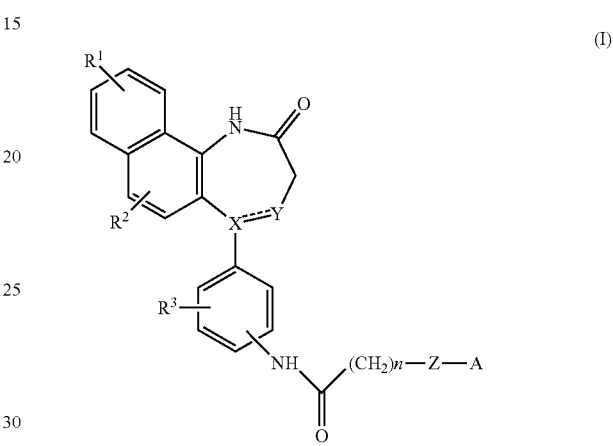

(I)

wherein, in the formula, R$^1$, R$^2$ and R$^3$ may be the same or different, and represent hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, or a dialkylamino group having 2 to 8 carbon atoms, X represents C or N, Y represents N or C(=O), provided that when X is C, Y represents N, and when X is N, Y represents C(=O), the double line consisting of the solid line and the broken line represents a single bond or double bond, n represents an integer of 0 to 6, Z represents O, S, or an atomic bond, and A represents pyridine ring having the same or different 1 to 5 substituents selected from N(R4)(R5), as a substituent, wherein R4 and R5 may be the same or different, and represent an alkyl group having 1 to 8 carbon atoms.

2. The compound according to claim 1, a tautomer or a stereoisomer of the compound, or a pharmacologically acceptable salt thereof, wherein R$^1$ represent hydrogen atom.

3. The compound according to claim 1, a tautomer or a stereoisomer of the compound, or a pharmacologically acceptable salt thereof, wherein R$^1$ represent hydrogen atom.

4. The compound according to claim 1, a tautomer or a stereoisomer of the compound, or a pharmacologically acceptable salt thereof, wherein $R^3$ represent hydrogen atom.

5. The compound according to claim 1, a tautomer or a stereoisomer of the compound, or a pharmacologically acceptable salt thereof,
wherein n represents an integer of 0.

6. The compound according to claim 1, a tautomer or a stereoisomer of the compound, or a pharmacologically acceptable salt thereof,
wherein Z represents an atomic bond.

7. The compound according to claim 1, a tautomer or a stereoisomer of the compound, or a pharmacologically acceptable salt thereof,
wherein A is pyridine ring having a dialkylamino group having 2 to 8 carbon atoms, as a substituent.

8. The compound according to claim 1, a tautomer or a stereoisomer of the compound, or a pharmacologically acceptable salt thereof,
wherein A is pyridine ring having a dimethylamino group, as a substituent.

9. The compound according to claim 1, a tautomer or a stereoisomer of the compound, or a pharmacologically acceptable salt thereof, wherein the compound is selected from the group consisting of the following (14) to (17) and (22):

(14) 2-(dimethylamino)-N-[4-(2,4-dioxo-2,3-dihydro-1-H-naphtho[1,2-b][1,4]diazepin-5(2H)-yl)phenyl]nicotinamide hydrochloride;

(15) 2-(dimethylamino)-N-[4-(2-oxo-2,3-dihydro-1H-naphtho[1,2-e][1,4]diazepin-5-yl)phenyl]nicotinamide dihydrochloride;

(16) 2-(dimethylamino)-N-[4-(2-oxo-2,3-dihydro-1H-naphtho[1,2-e][1,4]diazepin-5-yl)phenyl]nicotinamide dihydrochloride;

(17) 2-(dimethylamino)-N-[4-(2-oxo-2,3-dihydro-1H-naphtho[1,2-e][1,4]diazepin-5-yl)phenyl]nicotinamide dimethanesulfonate; and

(22) 4-(dimethylamino)-N-[4-(2-oxo-2,3-dihydro-1H-naphtho[1,2-e][1,4]diazepin-5-yl)phenyl]nicotinamide dihydrochloride.

10. A pharmaceutical composition comprising an effective amount of the compound according to claim 1 and at least one pharmaceutically acceptable carrier.

11. A method of treating nociceptive pain, inflammatory pain, or neuropathic pain comprising administering a composition containing the compound according to claim 1, a tautomer or a stereoisomer of the compound, or a pharmacologically acceptable salt thereof, to a subject in need of such treatment.

* * * * *

UNITED STATES PATENT AND TRADEMARK OFFICE
CERTIFICATE OF CORRECTION

PATENT NO. : 10,472,333 B2
APPLICATION NO. : 16/039947
DATED : November 12, 2019
INVENTOR(S) : S. Sakuma et al.

Page 1 of 1

It is certified that error appears in the above-identified patent and that said Letters Patent is hereby corrected as shown below:

In the Specification

Column 3, Line 11, please change "55.62" to -- 55 – 62 --
Column 4, Line 16, please change "I represents" to -- Y represents --

In the Claims

Column 32, Line 62 (Claim 2, Line 3), please change "represent hydrogen" to -- represents hydrogen --
Column 32, Line 66 (Claim 3, Line 3), please change "represent hydrogen" to -- represents hydrogen --
Column 33, Line 3 (Claim 4, Line 3), please change "represent hydrogen" to -- represents hydrogen --
Column 33, Line 55 (Claim 1, Line 25), please change "N(R4)(R5)" to -- $N(R^4)(R^5)$ --
Column 33, Line 56 (Claim 1, Line 26), please change "R4 and R5" to -- $R^4$ and $R^5$ --
Column 33, Line 66 (Claim 3, Line 3), please change "$R^1$" to -- $R^2$ --

Signed and Sealed this
Eighteenth Day of February, 2020

Andrei Iancu
*Director of the United States Patent and Trademark Office*